(12) United States Patent
Cowden

(10) Patent No.: US 6,294,521 B1
(45) Date of Patent: *Sep. 25, 2001

(54) PHOSPHOSUGARS AND PHOSPHOSUGAR-CONTAINING COMPOUNDS HAVING ANTI-INFLAMMATORY ACTIVITY

(75) Inventor: William Butler Cowden, Kambah (AU)

(73) Assignee: Australian National University (AU)

( * ) Notice: Subject to any disclaimer, the term of this patent is extended or adjusted under 35 U.S.C. 154(b) by 0 days.

This patent is subject to a terminal disclaimer.

(21) Appl. No.: 08/953,305

(22) Filed: Oct. 17, 1997

(30) Foreign Application Priority Data

Oct. 18, 1996 (AU) .................................................. PO 3098

(51) Int. Cl.[7] ............................ A61K 31/70; C07H 15/04
(52) U.S. Cl. .............................. 514/23; 514/25; 514/825; 514/885; 536/4.1; 536/117; 536/120; 536/123.13
(58) Field of Search ............................... 514/23, 25, 805, 514/885; 536/117, 4.1, 120, 123.13

(56) References Cited

FOREIGN PATENT DOCUMENTS

WO 90/01938    3/1990   (WO).

OTHER PUBLICATIONS

Ichikawa et al., Synthesis of Branched Glycopeptide derivative, Carb. Res., v. 198, pp. 235–246, 1990.*

Morten Meldal, et al., "Large–scale synthesis of D–mannose 6–phosphate and other hexose 6–phosphates", Carbohydrate Research, 235 (1992) 115–127.

* cited by examiner

*Primary Examiner*—Gary Geist
*Assistant Examiner*—Howard V. Owens, Jr.
(74) *Attorney, Agent, or Firm*—Fulwider Patton Lee & Utecht, LLP

(57) ABSTRACT

D-mannoside-6-phosphate compounds having anti-inflammatory activity are disclosed, and use thereof in treating inflammatory diseases, particularly cell-mediated inflammatory diseases.

17 Claims, No Drawings

PHOSPHOSUGARS AND PHOSPHOSUGAR-CONTAINING COMPOUNDS HAVING ANTI-INFLAMMATORY ACTIVITY

FIELD OF THE INVENTION

The present invention relates to novel phosphosugars and novel phosphosugar containing compounds that possess anti-inflammatory properties, and in particular it relates to the use of these compounds in the treatment of cell-mediated inflammatory diseases in animals and man.

BACKGROUND OF THE INVENTION

International Patent PCT/AU89/00350 (WO 90/01938) incorporated herein by reference, discloses certain phosphosugars and phosphosugar containing compounds as potent anti-inflammatory agents, and the use of these compounds as anti-inflammatory agents in animals and man. In particular, mannose-6-phosphate was shown to have anti-inflammatory activity against cell-mediated inflammatory diseases such as experimental autoimmune encephalomyelitis, adjuvant-induced artries and delayed type hypersensitivity in experimental animals.

In the work leading to the present invention, the inventors have found novel derivatives of mannose-6-phosphate and other phosphosugars which have more potent anti-inflammatory activity than phosphosugar compounds previously identified, and many of these novel compounds have pharmacological and physicochemical properties that are superior to those of the simple phosphosugars. These agents function by binding to certain receptor molecules (for example the mannose-6-phosphate receptor(s) or tile insulin-like growth factor II receptor), on the surface and/or inside cells, for which mannose-6-phosphate is an integral part of a natural ligand. These agents, when present, can effectively inhibit the ability of inflammatory leukocytic cells to cause inflammation and can inhibit the pathological sequence associated with inflammation.

The mannose-6-phosphate receptor is a multifunctional receptor and, in addition to binding degradative enzymes to the cell surface (1), it can also bind certain cytokines and growth factors, such as transforming growth factor-beta (TGF-beta) (2) and insulin-like growth factor II (1,3), which may have roles in inflammation and its sequels TOF-beta is one of a superfamily of signaling molecules which play important roles in modulating cell growth (4). TGF-beta, is a potent fibrogenic cytokine, and thus is probably important in scar tissue formation (5) as an integral part of the inflammatory response. Thus, another part of the anti-inflammatory effect of mannose-6-phosphate-containing compounds is their potential to block the effects of cytokine and/or growth factors in inflammation by blocking their binding to the mannose-6-phosphate receptor. While it is not intended that the present invention should be restricted in any way by a theoretical explanation of the mode of action of the novel phosphosugars in accordance with the invention, it is presently believed that these active compounds may exert their anti-inflammatory effect by acting as antagonists or competitive inhibitors of the natural ligands of mannose phosphate receptors on and/or in cells.

Accordingly, the active novel phosphosugars and novel phosphosugar containing compounds include compounds which are effective as competitive inhibitors or antagonists of the cellular receptors for which mannose-6-phosphate is wholly or an integral part of the natural ligand.

SUMMARY OF THE INVENTION

In one aspect, the present invention provides novel derivatives of naturally occurring phosphosugars which have been found to be effective inhibitors of inflammation in experimental animals. These derivatives include D-mannose-6-phosphate derivatives of the general Formula I:

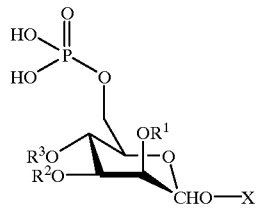

wherein the mannose-6-phosphate residue as shown in Formula I can be in either the α configuration or the β configuration. Formula I thus may represent a 1—O—X-substituted α- or β-D-mannose-6-phosphate or a mixture of these and, where X is not hydrogen, such compounds are known as mannoside 6-phosphates. When $R_1$, $R_2$, $R_3$ and X all represent hydrogen atoms, Formula I represents the chemical structure of D-mannose-6-phosphate.

Referring to Formula I, X may be selected from among the following functional groups, which may optionally be substituted: aliphatic hydrocarbon, saturated or unsaturated, branched or straight chain; cyclic aliphatic hydrocarbons, saturated or unsaturated; aryl; heteroaryl; aralkyl; heteroaralkyl; polyether; and monosaccharide, disaccharide or trisaccharide. $R_1$, $R_2$ and $R_3$, which may be the same or different, may be selected from hydrogen or an ester group, particularly an ester group such as acetyl, which may optionally be substituted.

Where X in Formula I is straight chain or branched alkyl, the alkyl chain may be from 1 to 20 carbon atoms inclusive. Where X is alkenyl or alkynyl, the carbon chain may be straight or branched and may be from 2 to 20 carbon atoms inclusive. The optional substituents for these aliphatic chains may be selected from among the following functional groups: trichloromethyl; trifluoromehyl; cyclopropyl; cyclobutyl; cyclopentyl; cyclohexyl; cycloheptyl; methoxy; ethoxy; propoxy; iso-propoxy; butoxy; sec-butoxy; isobutoxy; phenoxy; benzyloxy; oxo; hydroxy; thio; methythio; fluoro; chloro or bromo. Where X is cycloalkyl, it may be selected from among the following: cyclopropyl; cyclobutyl; cyclopentyl; cyclohexyl and cycloheptyl. Where X is aryl, it may be selected from among the following: phenyl or naphthyl, and this group may be variously substituted with from among the following moieties: hydrogen, methyl, ethyl, 2-propyl, methylenedioxy, fluoro, chloro, bromo, iodo, trichworomethyl; tritluoromethyl, methoxy; ethoxy; propoxy; iso-propoxy; butoxy,; sec-butoxy; isobutoxy; phenoxy; benzyloxy; hydroxy; thio; methylthio; carboxy; carboxymethyl and carboxyethyl. Where X is heteroaryl, it may be selected from among the following: pyridyl; thiophenyl; furyl; pyrimidinyl; benzimidazolyl; sym-triazinyl, asym-triazinyl; thiazolyl and thiadiazolyl, and these groups may be variously substituted with from among the following moieties; hydrogen, methyl, ethyl, 2-propyl, methylenedioxy, fluoro, chloro, bromo, iodo, trichloromethyl; trifluoromethyl, methoxy; ethoxy; propoxy; iso-propoxy; butoxy; sec-butoxy; isobutoxy; phenoxy; benzyloxy; hydroxy; thio; methylthio; carboxy; carboxymethyl and carboxyethyl. Where X is aralkyl, it may be selected from among the following: methylaryl; ethylaryl; 2- or 3-propylaryl; 2-, 3- or 4-butylaryl or 2-, 3-, 4- or 5-pentylaryl wherein the aryl group may be selected from among the following: phenyl; naphthyl; phenanthrenyl and anthracenyl, and these aryl groups may be variously substituted with from among the following moieties hydrogen, methyl, ethyl, 2-propyl, methylenedioxy, fluoro, chloro, bromo, iodo, trichloromethyl; trifluoromethyl, methoxy; ethoxy; propoxy; iso-propoxy; butoxy; sec-butoxy; isobutoxy; phenoxy; benzyloxy; hydroxy; thio; methylthio; carboxy; carboxymethyl and carboxyethyl. Where X is heteroaralkyl, it may be selected from among the following: methylheteroaryl; ethylheteroaryl; 2- or 3-propylheteroaryl; 2-, 3- or 4-butylheteroaryl or 2-, 3-, 4-, or 5-pentylheteroayl wherein the heteroaryl group may be selected from among the following: pyridyl; thiophenyl; furyl; pyrimidinyl; benzimidazolyl; sym-triazinyl; asym-triazinyl; thiazolyl and thiadiazolyl, and these heteroaryl groups may be variously substituted with from among the following moieties: hydrogen, methyl, ethyl, 2-propyl, methylenedioxy, fluoro, chloro, bromo, iodo, trichloromethyl; trifluoromethyl, methoxy; ethoxy; propoxy; iso-propoxy; butoxy; sec-butoxy; isobutoxy; phenoxy; benzyloxy; hydroxy; thio; methylthio; carboxy; carboxymethyl and carboxyethyl. Where X is polyether, it may be selected from among the following: polyethylene glycol up to 400 molecular weight (MW); methoxypolyethylene glycol up to 400 MW; polypropylene glycol up to 425 MW and methoxypolypropylene glycol up to 425 MW. Where X is a monosaccharide, disaccharide or trisaccharide it can be any such sugar group where the chemical link, as illustrated in Formula I, is through an oxygen atom.

As described above, in Formula I, $R_1$, $R_2$ and $R_3$ may represent either hydrogen or an ester group. A preferred ester group is acetyl, however $R_1$, $R_2$ and $R_3$ may also be selected from the following functional groups: trichloroacetyl, trifluoroacetyl, propanoyl; butanoyl; 2-methylpropanoyl; pentanoyl; 2-methaylbutanoyl; 3-methylbutanoyl; trimethylacetyl; hexanoyl; 2-methylpentanoyl; 3-methylpentanoyl; 2,2-dimethylbutanoyl; heptanoyl; 2-methylhexanoyl; 3-methylhexanoyl; 4-methylhexanoyl; 2,2-dimethylpentanoyl; octanoyl; palmitoyl; stearoyl.

Where $R_1$, $R_2$ and $R_3$ in formula I are variously alkenoyl, these groups may be selected from among the following: propenoyl; 2-butenoyl; 3-butenoyl, 2-pentenoyl; 3-pentenoyl; 4pentenoyl; palmitoyl; oleoyl; linoleoyl.

Where $R_1$, $R_2$ and $R_3$ in Formula I are variously cycloalkanoyl, these groups may be selected from among the following: cyclopropanecarbonyl; cyclobutanecarbonyl; cyclopentanecarbonyl; cyclohexanecarbonyl and cycloheptanecarbonyl.

Where $R_1$, $R_2$ ad $R_3$ in Formula I are variously aroyl, these groups may be selected from among the following: benzoyl; naphthoyl.

Where $R_1$, $R_2$ and $R_3$ in Formula I are variously heteroaroyl, these groups may be selected from among the following: pyridinoyl; thiophenoyl; furoyl; pyrimidinoyl; benzimidazoyl; sym-triazinoyl; asym-triazinoyl; thiazoloyl and thiadiazoloyl.

A small number of D-mannose-6-phosphate derivatives having the general Formula I have been disclosed by Meldal et al. (27). In particular, compounds of the general Formula I wherein X is methyl, butyl or hexadecyl and $R_1$, $R_2$ and $R_3$ all represent hydrogen were disclosed by Meldal et al., however no activity, and in particular no anti-inflammatory activity, is disclosed for these compounds. Accordingly, the novel #D-mannose-6-phosphate derivatives of formula I of the present invention do not include the particular compounds wherein $R_1$, $R_2$ and $R_3$ are hydrogen and X is methyl, butyl or hexadecyl, although the present invention does extend to the use of these particular compounds as anti-inflammatory agents and in anti-inflammatory pharmaceutical compositions.

In yet another aspect, the present invention provides diphosphosugar compounds which are also potent anti-inflammatory agents.

Accordingly, the present invention also includes D-mannose-6-phosphate derivatives of the general Formula IA:

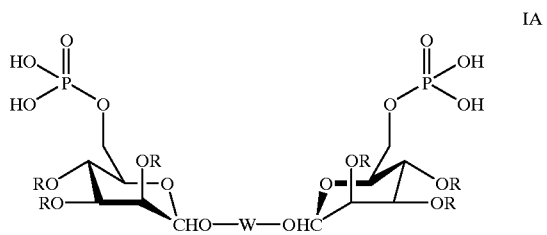

IA wherein
$R_1$, $R_2$ and $R_3$ are as defined above; and
W is a linker moiety between the residues.

Such diphosphosugar compounds include compounds comprising two phosphosugar residues of the general Formula I linked through either a flexible, semi-flexible or rigid linker between the phosophosugar residues General Formula II

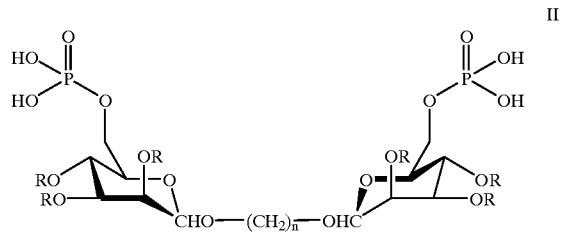

II represents a molecule containing two D-mannose-6-phosphate residues linked through oxygen atoms on their respective 1 positions and is representative of diphosphosugars which have a flexible straight chain hydrocarbon linker between the two phosphosugar residues. Each D-mannose-6phosphate residue can be in either the α- or β-configuration. The chain length of the flexible linker $(CH_2)_n$ is represented by the number of methylene groups comprising the hydrocarbon chain indicated by n, wherein n can be from 2 to 20 inclusive. In Formula II, R can be variously hydrogen, acetyl or may be selected from among those functional groups identified for $R_1$, $R_2$ and $R_3$ in Formula I above.

General Formula III

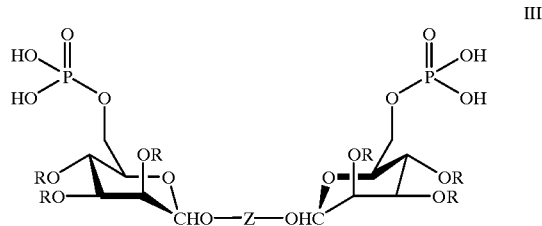

III is representative of a molecule containing two D-mannose residues linked with a rigid linker, Z, bound through the oxygen atoms on the respective 1 positions of each D-mannose-6-phosphate residue. Each D-mannose-6-phosphate residue can be in either the α- or β-configuration. Where the linker is aryl, it may be selected from phenyl or naphthyl, which may be variously substituted with from among the following moieties hydrogen, methyl, ethyl, 2-propyl, methylenedioxy, fluoro, chloro, bromo, iodo, trichloromethyl; tifluoromethyl, methoxy; ethoxy; propoxy; iso-propoxy; butoxy; sec-butoxy; isobutoxy; phenoxy; benzyloxy; hydroxy; thio; methylthio; carboxy; carboxymethyl and carboxyethyl. Where the linker is heteroaryl, it may be selected from among the following: pyridyl; thiophenyl; furyl; pyrimidinyl; benzimidazolyl; sym-triazinyl; thiazolyl, thiadiazlyl, quinolinyl, isoquinolinyl, cinnolinyl, quinazolnyl, 1,4-benzodiazinyl, pteridinyl, naphthyridinyl, pyrido[3,2-b], [3,4-b] or [4,3-b]pyridinyl, purinyl, acridinyl, phenoxazinyl, phenothiazinyl, carbazolyl, phenaznyl, 1,10-phenanthrolinyl, 4,7-phenanthrolinyl, etc., and these groups may be variously substituted with from among the following moieties: hydrogen, methyl, ethyl, 2-propyl, methylenedioxy, fluoro, chloro, bromo, iodo, trichioromethyl; trifluoromethyl, methoxy; ethoxy; propoxy; iso-propoxy; butoxy; sec-butoxy; isobutoxy; phenoxy; benyloxy; hydroxy; thio; methylthio; carboxy; carboxymethyl and carboxyethyl. In Formula III, R can be variously hydrogen, acetyl or may be selected from among those functional groups identified for $R_1$, $R_2$ and $R_3$ above.

General Formula IV

IV

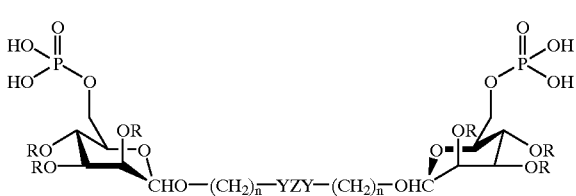

represents a molecule containing two D-mannose-6-phosphate residues linked through a flexible aralkyl linker attached at the oxygen atoms on the respective 1 positions of each D-mannose-6-phosphate residue. Z may be either aryl or heteroaryl, and n represents the number of methylene groups between each phosphosugar residue and the aryl or heteroaryl group, wherein n can be from 1 to 10 inclusive. Where the linker is aryl, it may be selected from phenyl or naphthyl, which may be variously substituted with from among the following moieties hydrogen, methyl, ethyl, 2-propyl, methylenedioxy, fluoro, chloro, bromo, iodo, trichloromethyl; trifluoromethyl, methoxy; ethoxy; propoxy; iso-propoxy; butoxy; sec-butoxy; isobutoxy; phenoxy; beneloxy; hydroxy; thio; methylthio; carboxy; carboxymethyl and carboxyethyl. Where the linker is heteroaryl, it may be selected from among the following: pyridyl; thiophenyl; furyl; pyrimidinyl; benzimidazolyl; sym-triazinyl; thiazolyl, thiadiazolyl, quinolinyl, isoquinolinyl, cinnolinyl, quinazolinyl, 1,4-benzodiazinyl, pteridinyl, naphthyridinyl, pyrido[3,2-b], [3,4-b] or [4,3-b]pyridinyl, purinyl, acridinyl, phenoxazinyl, phenothiazinyl, carbazolyl, phenazinyl, 1,10-phenantbrolinyl, 4,7-phenanthrolinyl, etc., and these groups may be variously substituted with from among the following moieties: hydrogen, methyl, ethyl, 2-propyl, methylenedioxy, fluoro, chloro, bromo, iodo, trichloromethyl; trifluoromethyl, methoxy; ethoxy; propoxy; iso-propoxy; butoxy; sec-butoxy; isobutoxy; phenoxy; benzyloxy; hydroxy; thio; methylthio; carboxy; carboxymethyl and carboxyethyl. In Formula IV, Y represents the point of attachment for the methylene chains to the aryl or the heteraryl group, and each Y may be selected from among the following: O, NH, S, CO, $CH_2$. Y can also be either COO or CONH wherein the carbonyl moiety (CO) is directly attached to the aryl or heteroaryl group. The D-mannose-6-phosphate residues attached through their 1-positions to the linker can be in either the α- or the β-configuration. In formula IV, R can be variously hydrogen, acetyl or may be selected from among these functional groups identified for $R_1$, $R_2$ and $R_3$ above.

The phosphosugar compounds of the present invention have potent anti-inflammatory activity, and as noted above it is believed that these active compounds may exert their anti-inflammatory effect by acting as antagonists or competitive inhibitors of the natural ligands of mannose phosphate receptors on and/or in cells.

Accordingly, in another aspect the present invention provides a method of treatment of inflammation, in particular cell-mediated inflammation, in a human or. animal patient in need of such treatment, which comprises administration to the patient of an effective amount of at least one phosphosugar derivative as broadly described herein, in particular at least one compound of general Formula I, IA, II, III or IV as described above.

In another aspect, there is provided a pharmaceutical or veterinary composition for anti-inflammatory treatment of a human or animal patient, which comprises at least one phosphosugar derivative as broadly described herein, in particular at least one compound of general Formula I, IA, II, III or IV as described above, together with an acceptable pharmaceutical or veterinary carrier or diluent therefor.

Finally, the present invention extends to the use of at least one phosphosugar derivative as broadly described herein, in particular at least one compound of general Formula I, IA, II, III or IV as described above, in the preparation of a pharmaceutical or veterinary composition for anti-inflammatory treatment of a human or animal patient.

The present invention also extends to methods for the preparation of the phosphosugar derivatives described herein. These methods are described in detail, by way of exemplification thereof, in the Examples below.

DETAILED DESCRIPTION OF THE INVENTION

The novel phosphosugars and phosphosugar-containing compounds of this invention have potent anti-inflammatory activity, in particular against cell-mediated inflammatory diseases such as experimental autoimmune encephalomyelitis and delayed type hypersensitivity in experimental animals.

Experimental auto-immune encephalomyelitis (EAE) is an inflammatory disease of the central nervous system which, because it has similarities to multiple sclerosis (MS), has often been used as an animal model of that disease (8,9, 10). The pathology of EAE is characterized by lymphocytic and mononuclear cell inflammation, an increase in blood-brain barrier permeability, and demyelination (11,12) resulting in partial or complete paralysis and in severe cases death of the affected animal. It is known that neural antigen-specific $CD4^+$ T lymphocytes appear to be the initiators of the response since in vivo depletion of $CD4^+$ T cells inhibits induction of EAE (13) and $CD^{4+}$ T cell lines and clones can passively transfer disease (14,15). Thus, the disease is characterised by its cell-mediated nature. Autoimmune enphalomyelitis, which occurs in man either as a result of vaccination or following viral infections of the central nervous system (also called post-infectious encephalomyelitis or acute disseminated encephalomyelitis), appears to be analogous to the actively-induced form of EAE in that it is characterised by infiltration of inflammatory cells into the central nervous system, breakdown of the blood brain barrier and demyelination resulting in, inter alia, partial or complete paralysis and in severe cases death (16,17). Like the animal model, antibodies against the neural antigen myelin basic protein, is found in patients who survive this disease (16,17).

International Patent PCT/AU89/00350 identified several simple phosphosugars which had potent anti-inflammatory activity against cell-mediated inflammatory diseases such as EAE. The novel mannose 6-phosphate derivatives of the present invention have improved pharmacodynamic and pharmacokinetic properties. Thus, some of these agents are effective against EAE when they are injected either subcutaneously or intraperitoneally in rats, whereas the parent substance, mannose-6-phosphate is ineffective when administered in this manner.

A variety of administration routes are available. The particular mode selected will depend, of course, upon the particular condition being treated and the dosage red for therapeutic efficacy. The methods of this invention, generally speaking, may be practised using any mode of administration that is medically acceptable, meaning any mode that produces therapeutic levels of the active component of the invention without causing clinically unacceptable adverse effects. Such modes of administration include oral, rectal, topical, nasal, transdermal or parenteral (e.g. subcutaneous, intramuscular and intravenous) routes. Formulations for oral administration include discrete units such as capsules, tablets, lozenges and the like. Other routes include intrathecal administration directly into spinal fluid, direct introduction such as by various catheter and balloon angioplasty devices well known to those of ordinary skill in the art, and intraparenchymal injection into targeted areas.

The compositions may conveniently be presented in unit dosage form and may be prepared by any of the methods well known in the art of pharmacy. Such methods include the step of bringing the active component into association with a carrier which constitutes one or more accessory ingredients. In general, the compositions are prepared by uniformly and intimately bringing the active component into association with a liquid carrier, a finely divided solid carrier, or both, and then, if necessary, shaping the product.

Compositions of the present invention suitable for oral administration may be presented as discrete units such as capsules, cachets, tablets or lozenges, each containing a predetermined amount of the active component, in liposomes or as a suspension in an aqueous liquor or non-aqueous liquid such as a syrup, an elixir, or an emulsion.

Compositions suitable for parenteral administration conveniently comprise a sterile aqueous preparation of the active component which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in polyethylene glycol and lactic acid. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono-or di-glycerides. In addition, fatty acids such as oleic acid find use in the preparation of injectables.

Other delivery systems can include sustained release delivery systems. Preferred sustained release delivery systems are those which can provide for release of the active component of the invention in sustained release pellets or capsules. Many types of sustained release delivery systems are available. These include, but are not limited to: (a) erosional systems in which the active component is contained within a matrix, and (b) diffusional systems in which the active component permeates at a controlled rate through a polymer. In addition, a pump-based hardware delivery system can be used, some of which are adapted for implantation.

Oral administration for many conditions will be preferred because of file convenience to the patient, although topical and localised sustained delivery may be even more desirable for certain treatment regimens.

The active component is administered in therapeutically effective amounts. A therapeutically effective amount means that amount necessary at least partly to attain the desired effect, or to delay the onset of, inhibit the progression of, or halt altogether, the onset or progression of the particular condition being treated. Such amounts will depend of course, on the particular condition being treated, the severity of the condition and individual patient parameters including age, physical condition, size, weight and concurrent treatment. These factors are well known to those of ordinary skill in the an and can be addressed with no more than routine experimentation. It is preferred generally that a maximum dose be used, that is, the highest safe dose according to sound medical judgement. It will be understood by those of ordinary skill in the art, however, that a lower dose or tolerable dose may be administered for medical reasons, psychological reasons or for virtually any other reasons.

The formulation of such therapeutic compositions is well known to persons skilled in this field. Suitable pharmaceutically acceptable carriers and/or diluents include any and all conventional solvents, dispersion media, fillers, solid carriers, aqueous solutions, coatings, antibacterial and antifungal agents, isotonic and absorption delaying agues, and the like. The use of such media and agents for pharmaceutically active substances is well known in the art, and it is described, by way of example, in *Remington's Pharmaceutical Sciences,* 18th Edition, Mack Publishing Company, Pennsylvania, USA. Except insofar as any conventional media or agent is incompatible with the active ingredient, use thereof in the pharmaceutical compositions of the present invention is contemplated. Supplementary active ingredients can also be incorporated into the compositions.

It is especially advantageous to formulate compositions in dosage unit form for ease of administration and uniformity of dosage. Dosage unit form as used herein refers to physically discrete units suited as unitary dosages for the human subjects to be treated; each unit containing a predetermined quantity of active ingredient calculated to produce the desired therapeutic effect in association with the required pharmaceutical carrier . and/or diluent. The specifications for the novel dosage unit forms of the invention are dictated by and directly dependent on (a) the unique characteristics of the active ingredient and the particular therapeutic effect to be achieved, and (b) the limitations inherent in the art of compounding such an active ingredient for the particular treatment.

Generally, daily oral doses of active component will be from about 0.01 mg/kg per day to 1000 mg/kg per day. Small doses (0.01–1 mg) may be administered initially, followed by increasing doses up to about 1000 mg/kg per day. In the event that the response in a subject is insufficient at such doses, even higher doses (or effective higher doses by a different, more localised delivery route) may be employed to Tee extent patient tolerance permits. Multiple doses per day are contemplated to achieve appropriate systemic levels of compounds.

Throughout this specification, unless the context requires otherwise, the word "comprise", or variations such as "comprises" or "comprising", will be understood to imply the inclusion of a stated integer or group of integers but not the exclusion of any other integer or group of integers."

Further features of the present invention are more fully described in the following Examples. It is to be understood, however, that this detailed description is included solely for the purposes of exemplifying the present invention, and should not be understood in any way as a restriction on the broad description of the invention as set out above.

In the accompanying drawing, FIG. 1 shows the effect of novel mannoside-6-phosphates on the uptake of fluorescein-labelled polysaccharide (PPME) by human U937 monocytes.

Preparation of Novel Phosphosugars:

Unless otherwise specified all chemical reagents were purchased from Aldrich Chemical Company. $^1$HNMR spectra were taken in $CDCl_3$ (TMS), $D_2O$ or $(CD_3)_2SO$ and obtained at 300 MHZ on a Gemini 300 NMR Spectrometer. 1,2,3,4-Tetra-O-acetyl-D-mannose and 1,2,3,4,6-penta-O-acetyl-D-mannose were prepared as described by Reynolds and Evans (6); 1-bromo-2,3,4,6-tetra-O-benzoylmannose was prepared by the method of Hudson et al. (7).

EXAMPLE 1

Preparation of 1-alkyl mannoside 6-phosphates.

Decyl 2,3,4-tri-O-acetyl-D-mannoside 6-phosphate (Formula I; $X=(CH_2)_9CH_3$, $R=COCH_3$)

A mixture of 1,2,3,4-tetra-O-acetyl-D-mannose (5.8 g), 1-decanol (3.9 g) and $ZnCl_2$ (2.9 g) was heated at 100–110° C. with stirring under reduced pressure, with a soda lime trap interposed between the reaction vessel and the vacuum source to remove acetic acid, for 4 hours. The resulting mass was dissolved in ethyl acetate (50 ml) and washed with water (2×20 ml) and dried over anhydrous $Na_2SO_4$. The ethyl acetate was removed under reduced pressure and the residue was chromatographed on a silica gel 60 chromatography column (2×50 cm); elution with $CH_2Cl_2$ gave a mixture of 1-decyl acetate and 1-decanol. Subsequent elution with $CHCl_3$ gave substantially pure decyl 2,3,4-tri-O-acetyl-D-mannoside (3.73 g; 57%). ($^1$Hnmr, $CDCl_3$, TMS: 0.88, t, 3H; 1.27, bs, 14H; 1.62, m, 2H; 1.99–2.12, m, 9H; 3.48–4.35, m, 6H; 4.79–5.34, m, 3H).

To a solution of decyl 2,3,4-tri-O-acetyl-D-mannoside (3.9 g) in dry pyridine (15 ml) was added diphenyl chlorophosphate (2.04 ml) dropwise at room temperature over 1 hour and the mixture allowed to stand at room temperature over night. The mixture was the heated at 40° C. for 3 h. The solvent was evaporated off under reduced pressure and the residue chromatographed on a silica gel chromatography column (silica gel 60; 2×60 cm). Initial fractions which were eluted with $CH_2Cl_2$ were discarded and subsequent elution with $CHCl_3$ gave decyl 2,3,4-tri-O-acetyl-D-mannoside 6-diphenylphosphate (4.0 g; 70%) in substantially pure form. ($^1$Hnmr, $CDCl_3$: 0.88, t, 3H; 127, broad s, 14H; 1.42, m, 2H; 1.99, s, 3H; 2.04, s, 3 H; 2.10, s, 3H; 3.2–4.4, m, 6H; 4.79, m, 1H; 5.2–5.5, m, 2H; 7.26, broad s, 10H).

Decyl 2,3,4-tri-O-acetyl-D-mannoside 6-diphenylphosphate (4.81 g), in dry methanol (50 ml), was hydrogenated in the presence of platinum oxide catalyst (0.5 g) at slightly greater than atmospheric pressure. When the calculated amount of hydrogen was taken up the catalyst was removed by filtration and the solvent evaporated under reduced pressure. The residue was chromatographed on a silica gel chromatography column (silica gel 60; 2.5×50 cm); initial fractions which were eluted with ethyl acetate were discarded and the fractions eluted subsequently with methanol contained the desired product. Thus, evaporation of methanol gave decyl 2,3,4-tri-O-acetyl-D-mannoside 6-phosphate (2.3 g; 63.8%). Calculated for $C_{22}H_{39}O_{12}P.2H_2O$; C 46.9%, H 7.65%, P 5.5%. Found C 46.7%, H 7.6%, P 5.4%. ($^1$Hnmr, $CDCl_3$: 0.88, t, 3H; 1.26, broad s, 14H; 1.54, broad m, 2H; 2.08–2.12, m, 9H; 2.10, s, 3H; 3.6–4.12, m, 6H; 4.76, m, 1H; 5.07–6.23, m, 2H).

Decyl D-mannoside 6-phosphate (Formula I; $X=(CH_2)_9CH_3$, $R=H$)

Decyl 2,3,4-tri-O-acetyl-D-mannoside 6-phosphate (2.3 g) in methanol (20 ml) was treated with 2N sodium methoxide (10.7 ml), the resulting solid filtered off and washed well with ethanol to give the disodium salt of decyl mannoside 6-phosphate (1.31 g), mp. 240° C. (decomp). (Calculated for $C_{16}H_{31}O_9Na_2P.3H_2O$: C, 38.8%, H, 7.2% P, 5.9%. Found; C, 38.6%, H, 7.4%, P, 6.2%). ($^1$Hnmr, $D_2O$: 0.7, t, 3H; 1.15, bs, 14H; 1.43, 2H; 3.3–4.0, nm, 7H).

In a similar manner the following novel mannoside 6-phosphates were prepared:

Pentyl 2,3,4-tri-O-acetyl-D-mannoside 6-phosphate (Formula I; $X=(CH_2)_4CH_3$, $R=COCH_3$); calculated for $C_{17}H_{29}O_{12}P$; C 44.7%, H 6.4%, P 6.8%. Found C 44.2%, H 6.8%, P 6.5%.

Pentyl D-mannoside 6-phosphate (Formula I; $X=(CH_2)_4CH_3$, $R=H$) disodium salt; calculated for $C_{11}H_{21}O_9PNa_2$; C 35.3%, H 5.7%., P 8.3%. Found C 35.0%, H 6.1%, P #8.0%.

Cyclohexylethyl 2,3,4-tri-O-acetyl-D-mannoside 6-phosphate (Formula I; $X=(CH_2)_2CH(CH_2)_5$, $R=COCH_3$); calculated for $C_{20}H_{33}O_{12}$ $P.H_2O$; C 46.7%, H 6.8%, P 6.0%. Found 46.7%, H 7.6%, P 6.2%.

Cyclohexylethyl D-mannoside 6-phosphate (Formula I; $X=(CH_2)_2CH(CH_2)_5$ $R=H$) disodium salt; calculated for $C_{14}H_{25}O_9PNa_2.1.5H_2O$; C 38.1%, H 6.4%, P 7.0%. Found C 38.2%, H 7.2%, P 6.8%.

EXAMPLE 2

A Further Method for Preparing cyclohexylalkyl mannose 6-phosphates.

Cyclohexylmethyl mannose 6-phosphate (FIG. 1; $X=(CH_2C_6H_{11}$, $R=H$).

A mixture of D-mannose (5.0 g), p-toluene sulphonic acid (0.18 g) and benzyl alcohol (10 ml) were heated at 100° C. for 2 hrs. The solution was diluted with ether (50 ml) and the upper layer decanted. The residue was recrystallised from ethyl acetate to give benzyl mannoside (2.5 g) mp 129° C. (lit 131–132° C.; Gorin and Perlin (28)). ($^1$Hnmr $CDCl_3$, 3.55, t, 1H; 3.65, m, 1H; 3.96, m, 1H; 4.14, m, 2H; 4.40, d, 1H; 4.52, d, 1H; 4.75, d, 1H; 4.96. s, 1H; 7.35, m, 5H.

To a solution of benzyl mannoside (1.66 g) and molecular sieve (A4, 0.5 g) in pyridine (30 ml) was added dropwise, with stirring, diphenyl chlorophosphate (1.3 ml). This mixture was allowed to warm slowly to room temperature and stand over night. The mixture was then heated at 40° C. for 1 hr. Saturated sodium bicarbonate (5 ml) was added to the cooled reaction mixture with stirring. The mixture was taken to dryness under reduced pressure. The residue was extracted with chloroform and chromatographed on silica gel 60 (2.0×30 cm). Elution with 10% chloroform in ethanol gave benzyl mannoside 6-diphenylphosphate (1.87 g).

($^1$Hnmr CDCl$_3$, TMS: 3.8, m, 2H; 3.85, m, 1H; 3.95, m 1H; 4.38–4.63, m, 4H; 4.89, s, 1H; 7.15–7.35, m, 15H).

Benzyl mannoside 6-diphenylphosphate (1.87 g) was hydrogenated at slightly above atmosphereic pressure in the presence of platinum oxide (0.15 g) in methanol (80 ml). After the uptake of hydrogen ceased the catalyst was filtered off and the solvent removed under reduced pressure to give the crude product (1.36 g). This product was dissolved in ethanol (30 ml) and 1N NaOMe (10 ml) was added. The resulting precipitate was filtered off and washed well with ethanol to give the disodium salt of cyclohexylmethyl mannoside 6-phosphate (1.08 g). ($^1$Hnmr D$_2$O: 0.7–0.83, m, 2H; 0.9–1.15, m, 2H; 1.35–1.63, m, 7H; 3.17, m, 1H; 3.32, m, 1H; 3.62, m, 1H, 3.65–3.76, m, 2H; 3.77–4.1, m, 2H; 4.66, d, 1H).

In a similar manner cyclohexylethyl mannoside 6-phosphate, identical with that described in Example 1, was prepared from phenylethyl mannoside 6-diphenylphosphate, the preparation of which follows.

Phenylethanol (280 mg), tetamethylurea (260 mg) and silver tifluorometbane sulfonate (591 mg) were dissolved in dichloromethane (15 ml) and stirred under nitrogen over molecular sieve (4A, 0.5 g) for 1 hr; then cooled to –18° C. and a solution of 1-bromo-2,3,4,6-tetra-O-benzoylmannose (1.43 g) in dichloromethane (10 ml) was added dropwise. The mixture was stirred at –18° C. for 4 hr and allowed to warm to room temperature and stirring was continued over night. The mixture was filtered through celite and the filtrate poured into cold water (15 ml), the organic layer was separated and washed successively with 10 ml volumes of saturated sodium bicarbonate solution, water, HCl (1M), water, saturated bicarbonate, water, then dried and the solvent removed under reduced pressure. Column chromatography of the residue on silica gel 60 (2.5×50 cm) and elution with 5.1 cyclohexane/ethyl acetate gave phenylethyl 2,3,4,6-tetra-O-benzoylmannoside (1.2 g, 85.7%). ($^1$Hnmr, CDCl$_3$: 2.8–2.9, m, 3H; 3.3, d, 1H; 3.65, m, 2H; 3.8–3.95, m, 4H; 4.82, s, 1H; 7.15–7.3, m, 25H). To this compound (1.1 g) in acetone (10 ml) and methanol (20 ml) was added sodium methoxide 1M (4 ml) and the m e stirred at room temperature for 2 hrs and then altered through celite, concentrated and the residue purified by column chromatography (2×40 cm silica gel 60). This was eluted with 27:2:1 ethylacetate-methanol-water to give phenylethyl mannoside (0.41 g) ($^1$Hnmr, CDCl$_3$: 2.8–2.87, m, 3H; 3.2, d, 1H; 3.65, m, 21; 3.8–3.95, m, 4H; 4.82, s, 1H; 7.15–7.3, m, 5H).

To a solution of phenylethyl mannoside (0.5 g) in pyridine (20 ml) at 0° C. was added diphenyl chlorophosphate (0.4 ml) dropwise, with stirring. The mixture was allowed to warm slowly to room temperature and stirred over night. After filtering, the pyridine was evaporated off under reduced pressure and the residue was chromatographed on a silica gel 60 column (2×60 cm). Elation with CHCl$_3$ separated unreacted diphenyl chlorophosphate and elution with 10% acetone/CHCl$_3$ gave phenylethyl D-mannoside 6-diphenylphosphate (0.64 g). ($^1$Hnmr, CDCl$_3$: 3.8, m, 2H; 3.27, d, 1H; 3.56–3.8, m, 4H; 3.88, d, 1H; 4.2, t, 1H; 4.451, t, 1H; 4,76, d, 1H; 7.2–7.4, m, 5H). Further elution of the chromatography column with 20% MeOH/CHCl$_3$ gave the starting mannoside (0.2 g).

EXAMPLE 3

Preparation of 1-aryl mannoside 6-phosphates.

Phenyl D-mannoside 6-phosphate (Formula I; X=C$_6$H$_5$, R=H).

1,2,3,4-Tetra-O-acetylmannose (10 g), phenol (9.0 g) and zinc chloride (1.0 g) were heated with tetramethylene sulfone (10 g) under reduced pressure at 120° with stirring for 1 h. The mixture was dissolved in CHCl$_3$ (100 ml) and washed with water and dried over anhydrous Na$_2$SO$_4$. After filtration the solvent was removed under reduced pressure and the residue was recrystalised from ethanol to give phenyl 2,3,4-tri-O-acetylmannoside (8.3 g, 67%), mp. 76–80° C. (lit syrup; Wang et al. (29)). Calculated for C$_{18}$H$_{22}$O$_9$; C, 56.5%; H 5.8%. Found: C 56.4%; H 5.6%.

Dibenzyl chlorophosphate was prepared by adding N-chlorosuccinimide (1.28 g) to a stirred solution of dibenzylphosphite (2.5 g) in benzene (100 ml) at room temperate. After 2 hrs at room temperature the solid (succinimide) was filtered off and the filtrate concentrated to about 5 ml, which was added dropwise to a solution of phenyl 2,3,4-tri-O-acetyl-D-mannoside (3.3 g) in dry pyridine (15 ml) at 0° C. with sting over 1 hour and the mixture allowed to stand at room temperature over night. The mixture was then heated at 40° C. for 2 hours. The solvent was evaporated off under reduced pressure and the residue chromatographed on a silica gel column (silica gel 60; 2.5×50 cm). Initial fractions eluted with methylene chloride were discarded and subsequent elution with ehloroform gave phenyl 2,3,4-tri-O-acetyl-D-mannoside 6-dibenzylphosphate (2.6 g). Calculated for C$_{32}$H$_{35}$O$_{12}$P.2H$_2$O; C, 56.6%; H, 5.8%. Found: C, 56.7%; H, 5.8%.

Phenyl 2,3,4-tri-O-acetyl-D-mannoside 6-dibenzylphosphate (2.6 g) in methanol (80 ml) was hydrogenated in the presence of 10% palladium on charcoal (0.3 g) at slightly greater tan atmospheric pressure until the appropriate amount of hydrogen was taken lip, after which the catalyst was removed by filtration and sodium hydride (0.4 g; 50% dispersion) was added to the filtrate. The mixture was concentrated to ca. 20 ml and diluted with ethanol (10 ml). The resulting precipitate was filtered off and washed with cold ethanol to give the desired disodium salt of phenyl mannoside 6-phosphate (0.74 g). Calculated for C$_{12}$H$_{15}$ON$_{12}$P; C 37.9%; H 4.0%. Found C 37.4%; H 5.4%. ($^1$Hnmr, D$_2$O: 3.5–3.65, m, 4H; 3.88, m, 1H; 4.0, m, 1H; 5.47, d, 1H; 6.96–7.04, m, 311; 72–7.28, m, 2H).

4'-Methoxyphenyl D-mannoside 6-phosphate (Formula I; X=p—C$_6$H$_4$OCH$_3$, R=H).

1,2,3,4Tetra-O-acetylmannose (6.0 g), 4-methoxyphenol (4.2 g), zinc chloride (0.6 g) and tetramethylenesulfone (6.0 g) were heated at 95° C. for 5 hours under reduced pressure. After cooling to room temperature, chloroform (100 ml) was added to the reaction mixture and the solution washed with water (3×30 ml) and dried over anhydrous sodium sulfate. After filtration, the solution was concentrated to a volume of 30 ml and chromatographed on a silica gel 60 column (2.5×60 cm). The column was eluted with chloroform to give 4-methoxyphenol which was discarded. Elution with 20% acetone/CHCl$_3$ gave 4'-methoxyphenyl 2,3,4-tri-O-acetyl-D-mannoside (4.6 g). ($^1$Hnmr, CDCl$_3$: 2.04, s, 3H; 2.1, s, 3H; 2.15, s, 3H; 3.7, s, 3H; 4.2, m, 1H; 4.25, m, 1H; 4.55, m, 1H; 5.0, d, 1H; 5.25, m, 1H; 5.4, m, 2H; 6.8, d, 2H; 6.95, d, 2H).

Dibenzyl chlorophosphate was prepared by adding N-chlorosuccinimide (2.2 g) to a solution of dibenzylphosphite (4.4 g) in dry toluene (70 ml) at room temperature with stirring. The resulting solid was filtered off and the filtrate concentrated to ca. 10 ml. and added to a solution of 4'-methoxyphenyl 2,3,4-tri-O-acetylmannoside (3.86 g) in pyridine (30 ml) at 0° C. and the mixture allowed to stand over night. The mixture was warmed to 40° C. for 1 h and the solvent evaporated under reduced pressure. The residue was chromatographed on a silica gel 60 chromatography column (2.5×55 cm). The column was first eluted with CHCl$_3$ and this fraction discarded. Subsequent elution with 20% acetone/CHCl$_3$ gave 4'-methoxyphenyl 2,3,4-tri-O-acetylmannoside dibenzylphosphate (2.9 g). (1Hnmr, CDCl$_3$: 2.06, s, 3H; 2.09, s, 3H; 2.13, s, 3H; 3.53, t, 1H; 3.6, s, 3H; 3.88, t, 1H; 3.97, m, 1H; 4.8, d, 1H; 5.12, m, 1H; 5.3, m, 2H; 6.81, d, 2H; 6.97, d, 2H; 7.3, m, 10H.) Starting material (1.46 g) was recovered from the column by elution with 10% EtOH/CHCl$_3$.

4'-Methoxyphenyl 2,3,4-tri-O-acetylmannoside dibenzylphosphate (2.9 g) and 10% Pd/C (0.3 g) in EtOH (50 ml) were shaken under hydrogen at slightly greater than atmospheric pressure until the absorption of hydrogen ceased. The catalyst was filtered off and the filtrate evaporated to dryness and the residue was dissolved in chloroform (20 ml) and chromatographed on a silica gel 60 chromatography column (2.5×60 cm). Elution with CHCl$_3$ gave a small amount (0.16 g) of an unidentified product which was discarded. Subsequent elution with MeOH gave a single product (2.1 g) which was dissolved in ether, insoluble material filtered off and the ether removed under reduced pressure. The residue was dissolved in methanol (20 ml) and 1 N sodium methoxide (9 ml) was added and the mixture diluted with ethanol (50 ml). The resulting solid was filtered off and washed with cold ethanol to give 4'-methoxyphenyl D-mannoside 6-phosphate (0.75 g) as its disodium salt ($^1$Hnmr, D$_2$O: 3.68, s, 3H; 3.5–3.7, m, 4H; 3.8, m, 1H; 3.98, d, 1H; 5.28, d, 1H; 6.77, d, 2H; 6.94, d, 2H).

A novel alternative method for preparation of alkyl, aryl and aralkyl mannoside 6-phosphates is disclosed in EXAMPLES 4, 5 and 6. In this alternative method when an alkyl, aryl or aralkyl mannoside was employed as starting material, it was found that there was no need to use O-protecting groups, such as acetyl or benzoyl, on the oxygen atoms at positions 2, 3 and 4 prior to reacting with the phosphorylating agent, diphenyl chlorophosphate. Thus, providing there was either a 1-O-alkyl, 1-O-aryl or 1-O-aralkyl group present on the sugar moiety, such compounds were discovered to react smoothly with the phosphorylating agent, diphenyl chlorophosphate, giving the appropriate mannoside 6-diphenyl phosphate as a single product. Under the reaction conditions disclosed below, diphenyl chlorophosphate reacted only at the oxygen atom at position 6 of the sugar, despite the absence of protecting groups on the oxygen atoms at positions 2, 3 and 4. This represents a novel and improved method over the procedure outlined above for the manufacture of mannoside 6-phosphates. Additionally, the new method offers a greatly simplified procedure for the preparation of alkyl mannoside 6-phosphates from commercially available alkyl mannoside staring materials. This novel method for preparation of mannoside 6-phosphates is illustrated in the examples that follow:

EXAMPLE 4

Methyl α-D-mannoside 6-phosphate (Formula I; X=CH$_3$, R=H)

To a solution of methyl α-D-mannoside (Aldrich Chemical Co)(1.94 g) in pyridine (20 ml) at <5° C. was added diphenyl chlorophosphate (2.1 ml) dropwise under an atmosphere of dry nitrogen. The reaction was allowed to stand at room temperature over night and then warmed to 50° C. for 2 hrs. After evaporating off the solvent under reduced pressure, water (50 ml) was added to the residue and the mixture extracted with CHCl$_3$ (100 ml). The CHCl$_3$ extract was washed with saturated NaHCO$_3$ solution (2×30 ml) and then water (2×30 ml) and dried over anhydrous Na$_2$SO$_4$. Filtration, followed by removal of the solvent under reduced pressure gave methyl α-D-mannoside 6-diphenylphosphate (1.9 g). ($^1$Hnmr, CDCl$_3$: 3.24, s, 3H; 3.7–3.9, m, 4H; 4.43–4.6, m, 2H; 4.66, s, 1H; 7.15–7.4, m, 10H).

Methyl α-D-mannoside 6-diphenylphosphate (1.6 g) and platinum oxide (0.16 g) in dry methanol (40 ml) were shaken under an atmosphere of hydrogen at slightly greater than atmospheric pressure for ca. 4 hrs. When the uptake of hydrogen ceased, the catalyst was removed by filtration and the solvent evaporated under reduced pressure to a volume of 10 ml. A solution of NaOCH$_3$ (0.4 g) in methanol (10 ml) was added to the above solution, a precipitate formed which was filtered off and washed with a small amount of cold MeOH to give the monosodium salt of methyl α-D-mannoside 6-phosphate (0.76 g; 63.9%). Calculated for C$_7$H$_{14}$O$_9$PNa; C, 28.4%; H, 4.7%; P, 10.5%; Na, 7.8%. Found: C, 28.5%; H, 5.0%; P, 10.4%; Na, 7.0%. The disodium salt, was prepared by stirring the monosodium salt in the presence of a slight excess of NaOH in methanol together with a few drops of water. The mixture was taken to dryness and the residue washed thoroughly with MeOH to give the expected disodium salt of methyl α-D-mannoside 6-phosphate. Calculated for C$_7$H$_{13}$O$_9$PNa$_2$.2H$_2$O; C, 25.0%; A, 4.5% P, 9.2%; Na, 13.7%. Found: C, 24.8%; H, 4.9%; P, 9.0%; Na, 13.2%.

EXAMPLE 5

Dodecyl D-mannoside 6-phosphate (Formula I; X=(CH$_2$)$_{11}$CH$_3$, R=H)

1-Dodecanol (1.3 g), tetraethylurea (0–7 g) and silver trifluoromethane sulfonate (1.6 g) were dissolved in dichloromethane (15 ml) and stirred in the presence of 4A molecular seive (1 g) for 1 hr under a dry nitrogen atmosphere. The mixture was then cooled to −18° C. To this stirred solution was added 1-bromo-2,3,4,6-tetra-O-benzoylmannose (3.65 g) in dichloromethane (10 ml), dropwise, while maintaining tie reaction temperature at −18° C. The reaction was stirred at this temperature for 4 hours, then allowed to wan slowly to room temperature and stirred over night. The mixture was filtered and added to cold water (20 ml). The organic phase was separated and washed successively with 10 ml volumes of saturated sodium bicarbonate, water, 1 M HCl, water, saturated bicarbonate, water and then dried over anhydrous sodium sulfate. After filtration, the mixture was concentrated to dryness and the residue purified by column chromatography (silica gel 60; 2.5×60 cm). The column was eluted with 4:1 petroleum spirit (bp 60–80° C.)-ethyl acetate to give dodecyl 2,3,4,6-tetra-O-benzoyl D-mannoside (2.6 g, 60%) as a syrup. ($^1$Hnmr CDCl$_3$: 0.9, t, 3H; 1.3, bs, 18H; 1.7, m, 24; 3.6, m, 1H;

3.85, m, 1H; 4.4–4.63, m, 2H; 4.7, dd, 1H; 5.1, d, 1H; 5.7, d, 1H; 5.94, dd, 1H; 6.13, t, 1H; 7.25–8.15, m, 10H).

Dodecyl 2,3,4,6-tetra-O-benzoyl n-mannoside (2.6 g) was dissolved in dry methanol (15 ml) and treated with sodium methoxide (1M, 3 ml) and this solution was, stirred over night. The resulting precipitate was filtered off and the solid dissolved in methanol and this solution was treated with Amberlite IR 120 (H$^+$ form). Filtration and evaporation gave dodecyl mannoside (0.85 g). The original filtrate was treated with Amberlite, filtered and evaporated and additional dodecyl mannoside (0.32 g) was isolated. ($^1$Hnmr, (CD$_3$)$_2$SO: 0.84, t, 314; 1.25, bs, 18H; 1.48, in, 2H; 3.24–3.65, m, 6H; 4.4–4.67, m, 3H).

A solution of dodecyl mannoside (0.67 g) in pyridine (20 ml) was cooled to 0° C. and diphenyl chlorophosphate (0.6 ml) was added dropwise, with stirring. The mixture was sired at room temperature over night. After filtering, the pyridine was evaporated and the residue was chromatographed on a silica gel 60 column (2.5×50 cm). Elution with CHCl$_3$ separated unreacted diphenylphosphoryl chloride and elution with 10% acetone/CHCl$_3$ gave dodecyl D-mannoside 6-diphenylphosphate (0.65 g). ($^1$Hnmr, CDCl$_3$: 0.9, t, 3H; 1.3, bs, 18H; 1.73, m, 2H; 3.36, m, 1;H 3.6, m, 1H; 3.7–3.9, m, 3H; 3.93, bs, 1H; 4.42, t, 1H; 4.66, m, 1H; 4.8, s, 1H; 7.2–7.4, m, 10H).

Dodecyl D-mannoside 6-diphenylphosphate (0.56 g) and Pt$_2$O (50 mg) in methanol (30 ml) were hydrogenated at slightly above atmospheric pressure. After uptake of hydrogen ceased the catalyst was removed by filtration, the filtrate was concentrated to 5 ml. An amorphous white solid was filtered off and discarded. 1 M sodium methoxide (3 ml) was added to the filtrate and after standing for 1 hour the resulting precipitate was filtered off and washed with ethanol to give the disodium salt of dodecyl D-mannoside 6-phosphate (75 mg). Calculated for C$_{18}$H$_{35}$O$_9$PNa$_2$.2H$_2$O; C, 45.3%; H, 8.2%; P, 6.5%. Found: C, 45.1%; H, 7.9%; P, 6.5%. ($^1$Hnmr, D$_2$O: 0.73, t, 3H; 1.2, bs, 18H; 1.42, bs, 2H ; 3.28–4.27, m, 8H, 4.9, s, 1H).

In a similar manner the following alkyl mannoside 6-phosphates were prepared:
1. Propyl D-mannoside 6-diphenylphosphate ($^1$Hnmr, CDCl$_3$: 0.83, t, 3H; 1.5, q, 2H; 3.25, q, 1H; 3.5, q, 1H; 3.73–3.84, m, 3H; 3.9, bs, 1H; 4.54, m, 2H; 4.76, s, 1H; 7.15–7.36, m, 10H) was hydrogenated to give propyl mannoside 6-phosphate (Formula 1; X=(CH$_2$)$_2$CH$_3$, R=H) disodium salt. Calculated for C$_9$H$_{17}$O$_8$PNa$_2$.H$_2$O; C, 30.4%, H, 5.1%, P, 8.7%. Found C, 30.9%, 1H 5.4%, P, 8.3% ($^1$Hnmr, D$_2$O: 0.76, t, 3H; 1.45, q, 2H; 3.33, m, 1H; 3.5, m, 2H; 3.6–3.83, in 4H; 3.9, m, 1H; 4.71 d, 1H).
2. Butyl D-mannoside 6-diphenylphosphate ($^1$Hnmr, CDCl$_3$: 0.83, t, 3H; 1.23, q, 4H; 1.5, m, 2H; 3.25, q, 1H; 3.5, q, 1H; 3.71–3.82, m, 3H; 3.9, bs, 1H; 4.53, m, 2H; 4.76, s, 1H; 7.15–7.36, m, 10H) was hydrogenated to give butyl mannoside 6phosphate Formula I; X=(CH$_2$)$_3$CH$_3$, R=H) disodium salt ($^1$Hnmr, D$_2$O: 0.77, t, 3H; 1.16, bs, 4H; 1.48, m, 2H; 3.35, m, 1H , 3.55, m, 2H; 3.61–3.8, m, 4H; 3.91, m, 1H; 4.71, d, 1H).
3. Hexyl D-mannoside 6-diphenylphosphate ($^1$Hnmr, CDCl$_3$: 0.85, t, 3H; 1.23, bs, 6H; 1.5, m, 2H; 3.3, q, 1H; 3.55, q, 1H; 3.70–3.84, m, 3H; 3.88, bs, 1H; 4.45, t 1H; 4.6, m, 1H; 4.76, s, 1H; 7.17–7.37, m, 10H) was hydrogenated to give hexyl D-mannoside 6-phosphate (Formula I; X=(CH$_2$)$_5$CH$_3$, R=H) disodium salt. ($^1$Hnmr, D$_2$O: 0.75, t, 3H; 1.15, bs, 6H; 1.47, q, 2H; 3.36, m, 1H; 3.56, m, 2H; 3.62–3.8, m, 4H; 3.92, m, 1H; 4.72, d, 1H).
4. Heptyl D-mannoside 6-diphenylphosphate ($^1$Hnmr, CDCl$_3$: 0.85, t, 3H; 1.23, bs, 8H; 1.5, m, 2H; 3.3, q, 1H; 3.55, q, 1H; 3.70–3.84, in, 3H; 3.88, bs, 1H; 4.45, t 1H; 4.6, m, 1H; 4.76, s, 1H; 7.17–7.37, m, 10H) was hydrogenated to give heptyl D-mannoside 6-phosphate (Formula I; X=(CH$_2$)$_6$CH$_3$, R=H) disodium salt. ($^1$Hnmr D$_2$O: 0.72, t, 3H; 1.23, m, 8H; 1.45, q, 2H; 3.34, m, 1H; 3.54, m, 2H; 3.6–3.78, m, 4H; 3.9, m, 1H; 4.7, d, 1H).
5. Hexadecyl D-mannoside 6-diphenylphosphate ($^1$Hnmr, CDCl$_3$: 0.85, t, 3H; 1.2, bs, 26H; 3.13, bs, 1H; 3.29–3.87, m, 6H; 4.41, t, 1H; 4.58, t with splitting, 1H; 4.74, s, 1H; 7.1–7.36, m, 10H) was hydrogenated to give hexadecyl D-mannoside 6-phosphate (Formula I; X=(CH$_2$)$_{15}$CH$_3$, R=H). Calculated for C$_{22}$H$_{43}$O$_9$P; C, 54.5%; H, 9.3%, P, 6.4%. Found: C, 54.5%; H, 11.1%; P. 6.4%. ($^1$Hnmr, CDCl$_2$: 1.23, t, 3H; 1.63, bs, 25H; 1.83, m, 2H; 3.63–4.43, m, 8H; 4.94, s, 1H).

EXAMPLE 6

Preparation of aralkyl mannoside 6phosphates.
Benzyl D-mannoside 6-phosphate (Figure. I: X=(CH$_2$C$_6$H$_5$, R=H)

To a mixture of chlorotrimethylsilane (7.1 ml) in pyridine (5.0 ml) was added benzyl mannoside (2.9 g) in small portions over 30 min at 0° C. with vigorous stirring. Stirring at 0° C. was continued for an additional 1.5 hr and the mixture was diluted with dichloromethane (15 ml) and allowed to stand over night Toluene (30 ml) was added and the mixture filtered. The filtrate was taken to dryness under reduced pressure at 30° C. and the residue was diluted with toluene (30 ml), filtered and the filtrate evaporated to dryness at 30° C. to give benzyl 2,3,4,6-tetra-O-trimethylsilylmannoside (5.58 g) as a syrup.

Benzyl 2,3,4,6-tetra-O-trimethylsilylmannoside (5.59 g) was dissolved in toluene (13 ml) and phosphoryl chloride (2 ml) in pyridine (2 ml) was added at room temperature. The mixture was warmed to 40° C. and stirred in the presence of molecular sieve (A4, 0.5 g) for 48 hrs. The mixture was filtered and the filtrate taken to dryness under reduced pressure at 35° C. Toluene (30 ml) was added to the residue and the resulting mixture was filtered. The filtrate was taken to dryness under reduced pressure to give benzyl 6-O-dichlorophosphoryl-1,2,3,4-tri-O-(trimethylsilyl)mannoside (5.58 g). This compound (5.58 g) was stirred with water (20 ml) for 30 minutes at 30° C. and then heated at 55° C. for 24 hours. The mixture was taken to dryness and water (20 ml) was added and after brief stirring the mixture evaporated to dryness under reduced pressure; this procedure was repeated twice. The crude residue was absorbed onto weakly basic ion exchange resin (DEAE Sephadex A-25; 9.0 g), this was washed well several times with water. The resin was then suspended in water (100 ml) and the pH adjusted to 9.0 with 1M NaOH solution. The resin was filtered off, washed with water and the filtrate taken to dryness under reduced pressure to give the disodium salt of benzyl mannoside 6-phosphate (0.73 g). ($^1$Hnmr, D$_2$O: 3.5–4.2, m, 6H; 4.47, d, 1H; 4.62, d, 1H; 4.87, d, 1H; 7.3, m, 5H).

Phenylethyl D-mannoside 6-phosphate (Formula I; X=(CH$_2$)$_2$C$_6$H$_5$, R=H)

To a mixture of chlorothiethylsilane (6.2 g) in pyridine (13.0 ml) was added phenylethyl mannoside (2.9 g) in small portions over 30 min at 40° C. with vigorous stirring. Stirring at 40° C. was continued for an additional 1.5 hr and the mixture was diluted with dichloromethane (15 ml) and allowed to stand over night. The precipitated pyridine hydrochloride was filtered off and washed with dichloromethane and the combined filtrates were evaporated to dryness. Toluene (30 ml) was added and the mixture filtered. The filtrate was taken to dryness under reduced pressure at 30° C. and the residue was diluted with toluene (30 ml), filtered and the filtrate evaporated to dryness at 30° C. to give phenylethyl 2,3,4,6tetra-tri-O-trimethylsilylmannoside (5.0 g)as a syrup. ($^1$Hnmr, CDCl$_3$: 0.05–0.25, m, 36H; 3.35, t, 2H; 3.3–3.9, m, 8H; 4.55, d, 1H; 7.1–7.2, m, 5H).

Phenylethyl 2,3,4,6-tetra-O-trimethylsilylmannoside (5.0 g) was dissolved in toluene (10 ml) and phosphoryl chloride (1.63 ml) in pyridine (1–6 ml) was added at room temperature. The mixture was warmed to 40° C. and stirred in the presence of molecular sieve (A4, 0.5 g) for 48 hrs. The mixture was filtered and the filtrate taken to dryness under reduced pressure at 35° C. Toluene (10 ml) was added to the residue and the resulting mixture was filter n-Pentane (151 ml) was added to the filtrate, cooled to 0° C. and this was extracted with 10 ml of a mixture consisting of HCl (37%, 0.5 ml), saturated sodium chloride solution (16.7 ml) and ice (33 ml). The organic layer was extracted twice more with saturated sodium chloride solution (5 ml). The organic layer was then dried over anhydrous magnesium sulfate, filtered and the pentane was removed under reduced pressure to give phenylethyl 6-O-dichlorophosphoryl-1,2,3,4-tri-O-(trimethylsilyl) mannoside (1.0 g). This compound (1.0 )

was stirred with water (5.0 ml) for 30 minutes at 30° C. and then heated at 55° C. for 24 hours, The mixture was taken to dryness and water (5.0 ml) was added and after brief stirring the mixture evaporated to dryness under reduced pressure; this procedure was repeated twice. The residue was absorbed onto weakly basic ion exchange resin DEAE Sephadex A-25; 5.0 g), this was washed well several times with water. The resin was ten suspended in water (30 ml) and the pH adjusted to 9.0 with 1M NaOH solution. The resin was filtered off, washed with water and the filtrate taken to dryness under reduced pressure to give the disodium salt of phenylethyl mannoside 6-phosphate (0.7 g) ($^1$Hnmr, $D_2O$: 2.8, t, 2H; 3.5–4.0, m, 8H; 5.1, d, 1H; 7.1–7.2, m, 5H).

By employing one or more of the above methods, other examples of alkyl D-mannoside 6-phosphates such as: ethyl, isopropyl, octyl and nonyl D-mannoside 6-phosphates can readily be prepared. In a similar manner aralkyl D-mannoside 6-phosphates such as variously substituted benzyl; variously substituted phenylethyl; phenylpropyl; variously substituted phenylpropyl; phenylbutyl; variously substituted phenylbutyl etc can be prepared. In a similar manner variously substituted aryl D-mannoside 6-phosphates such as: 3-methoxyphenyl; 2,3,5,6-tetramethyl-4-methoxyphenyl; 3-methylphenyl; 4-methylphenyl; 3-fluorophenyl; 4-fluorophenyl; 3-chlorophenyl; 4-chlorophenyl; 3,4-difluorophenyl; 3,4-dichlorophenyl and 3,4-dimethylphenyl etc can readily be prepared.

EXAMPLE 7

Preparation of Compounds of the Type Depicted in Formula II.

1,2-Ethylene di(D-mannoside 6-phosphate) (Formula II ; R=H, n=2)

Ethylene glycol (0.2 g), tetramethylurea (0.77 g) and silver trifluoromethane sulfonate (1.7 g) were dissolved in dichloromede (30 ml) and stirred in the presence of 4A molecular seive (1 g) for 1 hr under a dry nitrogen atmosphere. The mixture was then cooled to −18° C. To this stirred solution was added a solution of 1-bromo-2,3,4,6-tetra-O-benzoylmannose (4.35 g) in dichlorometane (10 ml) dropwise while maintaining the reaction temperature at −18° C. The reaction was stirred at this temperature for 4 hours and allowed to warm slowly to room temperature and stirred at this temperature over night. The mixture was filtered and added to cold water (20 ml). The organic phase was separated and washed successively with 15 ml volumes of saturated sodium bicarbonate, water, 1 M HCl, water, saturated bicarbonate, water and then dried over anhydrous sodium sulfate. After filtration, the mixture was taken to dryness under reduced pressure and tee residue pied by column chromatography (silica gel 60; 2×60 cm). Thus, the column was eluted with 3:1 petroleum ether (bp 60–80° C.)-ethyl acetate to give 1,2-ethylene 2,3,4,6-tetra-O-benzoyl D-mannoside (3.5 g). ($^1$Hnmr, $CDCl_3$: 3.85, d, 2H; 4.3, d, 2H, 4.8, in, 4H; 4.9, d, 2H; 5.25, s, 2H; 5.8, m, 2H; 6.1, m, 2H; 6.4, t, 2H; 7.1–8.3, m, 40H).

1,2-Ethylene 2,3,4,6-tetra-O-benzoyl D-mannoside (3.0 g) was dissolved in dry methanol (50 ml) and acetone (20 ml) and treated with sodium methoxide (1M, 10 ml) and this solution was allowed to stand over night This solution was then treated with Amberlite IR 120 (H$^+$ form), filtered and the filtrate taken to dryness to give 1,2-ethylene di(D-mannoside) (0.8 g). ($^1$Hnmr, $D_2O$: 3.45–3.77, m, 12H; 4.6–4.7, m, 6H).

To a solution of 1,2-ethylene di(D-mannoside) (0.6 g) in pyridine (10 ml), in the presence of molecular seive (4A; 0.5 g) was added diphenyl chlorophosphate (0.71 ml), dropwise, at 0° C. with stirring. The mixture was allowed to warm to room temperature and stir over night. The mixture was filtered and the filtrate was taken to dryness under reduced pressure. The residue was dissolved in chloroform (40 ml) and this was washed successively wit 10 ml volumes of water, saturated sodium bicarbonate solution and water. The organic layer was then dried over anhydrous sodium sulfate, filtered and taken to dryness to give 1,2-ethylene di(D-mannoside 6-diphenylphosphate) (0.4 g). ($^1$Hnmr, $CDCl_3$: 3.2, d, 2H; 3.48, d, 2H; 3.7, m, 2H; 3.85, bs, 6H; 4.42, m, 2H; 4.6, m, 2H; 4.7, d, 2H; 2H; 7.1–7.3, m, 20H).

1,2-Ethylene di(D-mannoside 6-diphenylphosphate) (0.37 g) was dissolved in dry MeOH (15 ml) and hydrogenated at slightly above atmospheric pressure in the presence of platinum oxide catalyst until uptake of hydrogen ceased. The catalyst was removed by filtration and the filtrate reduced to approximately 1 ml in volume. NaOMe, 1 N (1 ml) was added and the mixture diluted with ethanol (5 ml). The resulting precipitate was filtered off and washed well with dry ethanol to give the tetrasodium salt of 1,2-ethylene di(Dmannoside 6-phosphate) (0.17 g). Calculated for $C_{14}H_{24}O_{18}P_2Na_4$; C, 26.5%; H, 3.8%; P. 9.8%. Found C, 26.4%; H, 4.0%; P, 9.6%. ($^1$Hnmr, $D_2O$: 3.5–3.84, m, 12H; 4.6–4.77, m, The following compounds were made in a similar manner:

The tetrasodium salt of 1,6-hexamethyene di(D-mannoside 6-phosphate) (Formula II, R=H, n=6). Calculated for $C_{18}H_{32}O_{18}P_2Na_4.H_2O$; C 30.5%, H 4.8%, P 8.7%. Found, C 30.8, H 5.9%, P 8.5%. ($^1$Hnmr, $D_2O$: 1.4 bs, 4H; 1.62, m, 4H 3.52–3.94, m, 12H; 4.6–5.1, m, 6H).

The tetrasodium salt of 1,16-hexadecamethylene di(D-mannoside 6-phosphate) (Formula II; R=H, n=16). Calculated for $C_{28}H_{52}O_{18}P_2Na_4$; C 40.5%, H 6.3%, P 7.5%. Found C 40.1%, H 5.9%, P 7.3%. ($^1$Hnmr, $D_2O$: 1.23, bs, 24H; 1.45, m, 4H; 3.2–3.7, m, 12H; 4.4–4.91, m, 6H).

EXAMPLE 5

Preparation of Compounds of the Type Depicted in Formula III:

1,4-Phenylene di(D-mannoside 6-phosphate)

1,2,3,4,6-Penta-O-acetylmannose (12.0 g), 1,4-benzenediol (1.7 g), zinc chloride (1.2 g) and tetramethylenesulfone (10 g) were heated at 120° C. for 7 hrs under reduced pressure (water pump). After cooling to room temperature, the reaction mixture was dissolved in chloroform (100 ml) and washed with water (3×100 ml), dried over anhydrous sodium sulfate. Following filtration, the solvent was distilled off under reduced pressure and the residue chromatographed on a silica gel 60 column (3.0×35 cm). Elution with $CH_2Cl_2/CHCl_3$ (1:1) separated mainly tetramethylenesulfone (7.8 g). Elution with $CHCl_3$ yielded 1,4phenylene di(2,3,4,6-tetra-O-acetyl-D-mannoside) (4.0 g). ($^1$Hnmr, $CDCl_3$: 2.05, s, 6H; 2.07, s ,6H; 2.19, s, 6H; 2.21, s, 6H; 4.13, m, 6H; 4.3, q, 2H; 5.37, t, 2H; 5.45, s with splitting, 2H; 5.55, d with splitting, 2H; 7.05, s, 4E. Further elution with 5% acetone/$CH(Cl_3$ gave 4-hydroxyphenyl 2,3,4,6-tetra-O-acetylmannoside (3.55 g, 2621%) 1,4-Phenylene di(2,3,4,6-tetra-O-acetyl-D-mannoside) (4.0 g) was dissolved in dry methanol (30 ml) and acetone (20 ml) and treated with sodium methoxide (1M, 10 ml) and this solution was allowed to stand over night. This solution was then treated with Amberlite IR 120 (H$^+$ form), filtered and the filtrate taken to dryness to give 1,4-phenylene di(D-mannoside) (2.26 g). Found: C, 49.8; H, 5.5, $C_{18}H_{26}O_{12}$ requires C, 49.8; H, 6.0%. ($^1$Hnmr $D_2O$: 3.53–3.63, m, 8H; 3.82, m, 2H; 3.97, m, 2H; 5.33, d, 2H; 6.94, s. 4H).

To a mixture of chlorotrimethylsilane (0.6 ml) in pyridine (0.5 ml) was added 1,4-phenylene di(D-mannoside) (0.28 g)

in small portions over 30 min at 0° C. with vigorous stirring. Stirring at 0° C. was continued for an additional 1.5 hr and the mixture was diluted with dichloromethane (5.0 ml) and allowed to stand over night Toluene (5.0 ml) was added and the mixture filtered. The filtrate was taken to dryness under reduced pressure at 30° C. and the residue was diluted with toluene (5.0 ml), filtered and the filtrate evaporated to dryness at 30° C. to give 1,4phenylene di(2,3,4,6-tetra-O-trimethylsilyl-D-mannoside) (0.6 g).

1,4-Phenylene di(2,3,4,6-tetra-O-trimethylsilyl-D-mannoside) (0.6 g) was dissolved in toluene (20 ml) and phosphoryl chloride (0–24 ml) in pyridine (0.3 ml) was added at room temperature. The mixture was warmed to 40° C. and stirred for 24 hrs. The mixture was diluted with toluene (10 ml), filtered and the filtrate taken to dryness under reduced pressure at 30° C. The residue was extracted with toluene/petroleum spirit (bp 60–80° C.) 1:1 (20 ml) and the extracts filtered and taken to dryness under reduced pressure to give 1,4phenylene di(2,3,4-tri-O-trimethylsilyl-6-O-dichlorophosphoryl-D-mannoside) (0.6 g). This compound (0.6 g) was stirred with water (20 ml) at 30° C. for 30 min and then at 55° C. for 24 hours. The solution was taken to dryness and the residue dissolved in water (10 ml), stirred briefly and evaporated to dryness; this procedure was repeated three times. The residue was then dissolved in water (20 ml) and the resulting clear solution was mixed 15 with weakly basic anion exchange resin (DEAE Sephadex A-25; 5.0 g), this was filtered off and washed with water. The resin was then suspended in water (30 ml) and the pH adjusted to 9.0 with 1M NaOH solution. The resin was filtered off, washed with water (3×10 ml) and the combined filtrates taken to dryness under reduced pressure to give the disodium salt of 1,4-phenylene di(mannoside 6-phosphate) (0.2 g) ($^1$Hnmr, $D_2O$: 3.5–4.0, m, 12H; 5.05, s, 2H; 7.1, s, 4H).

In a similar fashion (2,3,5,6-tetramethyl)-1,4-phenylene di(D-mannoside 6-phosphate) (Formula III; R=H, Z=$C_6(CH_3)_4$) can be prepared.

EXAMPLE 9

Preparation of Compounds of the Type Depicted in Formula IV:

p-Phenylenebisoxyethyl di(D-mannoside 6-phosphate) (IV; R=H, Z=$C_6H_4$, Y=O, n=2);

1,4-Di(2'-hydroxyethoxy)benzene (0.56 g), tetramethylurea (0.67 g) and silver trifluoromethane sulfonate (1.49 g) were dissolved in dichloromethane (20 ml) and 1,2-dichloroethane (10 ml) and stirred in the presence of 4A molecular seive (1.5 g) for 1 hr under a dry nitrogen atmosphere. The mixture was then cooled to −18° C. To this stirred solution was added a solution of 1-bromo-2,3,4,6-tetra-O-benzoylmannose (3.76 g) in dichloromethane (15 ml) dropwise while maintaining the reaction temperature at −18° C. The reaction was stirred at this temperature for 4 hours and allowed to warm slowly to room temperature and stirred at this temperature over night. The mixture was filtered and added to cold water (25 ml). The organic phase was separated and washed successively with 30 ml volumes of saturated sodium bicarbonate, water, 1 M HCl, water, saturated bicarbonate, water and then dried over anhydrous sodium sulfate. After filtration, the mixture was taken to dryness under reduced pressure and the residue purified by column chromatography (silica gel 60; 2.5×70 cm). Thus, the column was eluted with 3:2 cyclohexane-ethyl acetate to give p-phenylenebisoxyethyl di(2,3,4,6-tetra-O-benzoyl D-mannoside) (2.0 g). ($^1$Hnmr, $CDCl_3$:4.0, m, 2H; 4.2, m, 4H; 4.4–4.8, m, 8H; 5.2, d, 2H; 5.75, d, 2H; 5.95, dd, 2H; 6.15, t, 2H; 6.95, s, 4H; 7.2–8.2, m, 40H).

p-Phenylenebisoxyethyl di(2,3,4,6-tetra-O-benzyl D-mannoside) (2.0 g) was dissolved in dry methanol (30 ml) and propan-2-ol (20 ml) and treated with sodium methoxide (1M, 10 ml) and this solution was stirred over night. This solution was then treated with Amberlite IR 120 ($H^+$ form), filtered and the filtrate taken to dryness to give p-phenylenebisoxyethyl di(D-mannoside) (0.6 g). ($^1$Hmnr, $(CD_3)_2SO$: 3.35–3.53, m, 8H; 3.6–3.75, m, 8H; 3.85, m, 2H; 4.05, m, 2H; 4.7, s, 2H; 6.87, s, 4H).

To a mixture of chlorotrimethylsilane (0.7 g) in pyridine (1.3 ml) was added p-phenylenebisoxyethyl di(D-mannoside) (0.6 g) in small portions over 30 min at 40° C. with vigorous stirring. Stirring at 40° C. was continued for an additional 1.5 hr and the mixture was diluted with dichloromethane (10 ml) and allowed to stand over night. The precipitated pyridine hydrochloride was filtered off and washed with dichloro methane and the combined filtrates were taken to dryness under reduced pressure at 30° C. The residue was diluted with toluene (10 ml), filtered and the filtrate evaporated to dryness at 30° C. to give p-phenylenebisoxyethyl di(2,3,4,6-tetra-O-trimethylsilylmannoside) (1.0 g) as a syrup.

p-Phenylenebisoxyethyl di(2,3,4,-tetra-O-trimethylsilylmannoside) (1.0 g) was dissolved in toluene (3 ml) and phosphoryl chloride (0.4 ml) in pyridine (0.5 ml). was added at room temperature. The mixture was warmed to 40° C. and stirred in the presence of molecular sieve (A4, 0.5 g) for 48 hrs. The mixture was filtered and the nitrate taken to dryness under reduced pressure at 35° C. Toluene (5 ml) was added to the residue and the resulting mixture was filtered. The filtrate was taken to dryness under reduced pressure to give p-phenylenebisoxy di(6-O-dichlorophosphoryl-1,2,3-tri-O-(trimethylsilyl)mannoside) (0.2 g). This compound (0.2 g) was stirred with water (1.0 ml) for 30 min at 30° C. and then heated at 55° C. for 24 hours. The mixture was taken to dryness and water (5 ml) was added and after brief stirring the mixture evaporated to dryness under reduced pressure; this procedure was repeated twice. The crude residue was absorbed onto weakly basic ion exchange resin (EAE Sephadex A-25; 5.0 g), this was washed well several times with water. The resin was then resuspended in water (30 ml) and the pH adjusted to 9.0 with 1M NaOH solution. The resin was filtered off; washed with water and the filtrate taken to dryness under reduced pressure to give the disodium salt of p-phenylenebisoxyethyl di(D-mannoside 6-phosphate) (0.1 g) ($^1$Hnmr; $D_2O$: 3.4–4.2, m, 22H; 5.1, d, 2H; 6.9, s, 4H).

The improved efficacy of the novel mannoside 6-phosphates is shown by comparison of the effect these agents have on the development of passively-transferred EAE in rats.

EXAMPLE 10

In this Example, some typical novel mannoside 6-phosphates of the present invention were compared with mannose-6-phosphate for their ability to inhibit the development of RAE in rats. In this experiment, according to the method of Panitch and McFarlin (18), donor Lewis rats were immunised with 50 μg myelin basic protein in complete Freund's adjuvant and 10–12 days later the spleens from these rats were removed and made into a single cell suspension. Thus, these cells, $2×10^6$ $ml^{-1}$, were cultured in RPMI medium with 5% fetal calf serum, $5×10^{-5}$ M 2-mercaptoethanol, 2 mM L-glutamine plus 30 μg/ml penicillin, 50 μg/ml streptamycin sulfate. Con A was added at 2 μg $ml^{-1}$ and cultures were incubated at 37° C. in a humidified atmosphere of 5% $CO_2$, 7% $O_2$ and the balance N$_2$. Cells were harvested after 72 hours, washed once wit Hanks balanced salt solution, and 70×10$^6$ viable cells were then transferred to naive Lewis rat recipients via a lateral tail vein in order to induce EAE.

The results of this experiment are shown in Table 1. Thus, the disodium salt of mannose-6-phosphate when given at a total dose of 220 mg/kg/day (724 μmoles/day) divided into equal subcutaneously injected doses 8 hourly for seven days was ineffective in inhibiting development of disease symptoms while the disodium salts of: decyl D-mannoside 6-phosphate given in a similar manner at a dose of 200 mg/kg/day (450 μmoles/day); hexadecyl D-mannoside 6-phosphate given in a similar manner at a dose of 200 mg/kg/day (379 μmoles/day) and 1,16-hexadecamethylene di(D-mannoside 6-phosphate) given in a similar manner at a dose of 200 mg/kg/day (241 μmoles/day) completely inhibited the development of disease. These results demonstrate the improved efficacy of the novel mannoside 6-phosphates over mannose-46-phosphate in treating inflammation of the central nervous system.

diagnostic tests such as the Mantoux test for tuberculosis. In the delayed-type sensitivity reaction the site of antigen deposition in the dermis becomes erythematous and induration can be seen within 6 hours of exposure to antigen. The erythema is due to vasodilation and the enduration is due to the influx of inflammatory cells. These clinical signs are maximal between 24 and 48 hours after challenge with antigen (21).

In this experiment sheep red blood cells were used as the antigen. Thus, groups of 5 male or female CBA mice were injected with cyclophosphamide (200 mg/kg ip) and one day later these mice were injected with sheep eythrocytes (1×10$^7$ in 200 μl of phosphate buffered saline). Five days later the mice were challenged by injecting sheep erythrocytes (1×10$^5$) into the left foot pad. The right foot pads of these mice served as controls and were therefore injected with phosphate buffered saline. Immediately following these injections the mice were treated with either the test agent or vehicle by subcutaneous injection in the flank and these injections were repeated four times at 8 hourly intervals

TABLE 1

Novel alkyl mannoside 6-phosphates are effective in treatment of experimental auto-immune encephatomyelitis when administered parenterally.

| Mannose 6-phosphate or control substances | dose mg/kg/day | Injections$^c$ | | Number of rats | % with clincial signs of EAE | Mean day of onset | Duration (days) | Mean Maximum clinical score |
|---|---|---|---|---|---|---|---|---|
| Saline control | — | t.i.d. | s.c. | 5 | 100 | 5.2 | 4.1 | 2.8 |
| PEG 200 vehicle control | — | t.i.d. | s.c. | 5 | 100 | 4.8 | 3.8 | 3.3 |
| mannose 6-P*$^a$ | 220 | t.i.d. | s.c. | 5 | 100 | 5.2 | 4.0 | 2.8 |
| hexadecyl mannoside 6-P$^b$ | 200 | t.i.d. | s.c. | 5 | 0 | — | — | 0 |
| decyl mannoside 6-P$^b$ | 200 | t.i.d. | s.c. | 5 | 0 | — | — | 0 |
| 1,16-hexadecamethylene di(D-mannoside 6-phosphate)** | 200 | t.i.d. | s.c. | 5 | 0 | — | — | 0 |

$^a$P = phosphate. *Administered as the disodium or **tetrasodium salts.
$^b$Administered in PEG 200.
$^c$Injection volume 100 μl.

International Patent PCT/AU89/00350 also identified simple phosphosugars which had anti-inflammatory activity in the delayed-type hypersensitivity reaction (DTH). To further demonstrate the improved efficacy of the novel mannoside 6-phosphates, these agents were compared with mannose-6-phosphate, for their effectiveness in treating DTH.

EXAMPLE 11

In this Example, the efficacy of some typical novel mannoside 6-phosphates of the present invention were compared with that of mannose-6-phosphate in the delayed-type hypersensitivity reaction (19,20,21) in mice. Delayed-type hypersensitivity is a cell-mediated inflammatory response against an antigen to which an individual has been. previously sensitised. This type of response is the basis of prior to measuring and comparing the swelling in the left foot pad (challenged) with that in the right foot pad (control) four hours after the last injection. Footpad diameters were measured with a dial guage calliper (AO2T; Schnelltaster, H. C. Kroplin GmbH, Schlüchtern, Hessen, Germany). The specific swelling was defined by subtracting the measurement of the left footpad (challenged) from that of the right footpad (control). Footpad thicknesses were measured to the nearest 0.05 mm The data obtained from this experiment are shown in Table 2. Analysis of the data showed that, when administered by subcutaneous injection, all of the novel mannoside 6-phosphates tested were found to be more effective against DTH in mice than mannose-6-phosphate, when administered in an identical manner.

TABLE 2

Novel mannoside 6-phosphates are effective in treatment of delayed type hypersentisivity (DTH) when administered parentally.

| Mannose 6-phosphate or control substances | dose mg/kg/day | Injections No. | site | Number of mice | % swelling | % inhibition of swelling[a] |
|---|---|---|---|---|---|---|
| Saline control | — | q.i.d. | s.c. | 5 | 100 | — |
| PEG 200 vehicle | — | q.i.d. | s.c. | 5 | 100 | — |
| mannose 6-phosphate* | 220 | q.i.d. | s.c. | 5 | 80 | 20 |
| hexadecyl mannoside 6-phosphate** | 200 | q.i.d. | s.c. | 5 | 20 | 80 |
| decyl mannoside 6-phosphate** | 200 | q.i.d. | s.c. | 5 | 30 | 70 |

*Administered as the disodium salt.
**Administered in PEG 200.
[a]Mean.

EXAMPLE 12

Contact sensitivity is a type of delayed hypersensitivity which ours following exposure to sensitising agents including low molecular weight reactive chemical entities such as dinitro chlorobenzene (DNCB) and picryl chloride (19,21) as well as the sensitising agents found in poison ivy and poison oak (19). In sensitised individuals, in those having previously been exposed to the sensitising agent, inflammatory leucocytes migrate from the blood stream into the area immediately beneath the affected tissue producing induration which is a cardinal characteristic of the delayed-type hypersensitivity reaction (21). Thus, contact sensitivity is a well recognised cell-mediated inflammatory response. In the experiment outlined below the novel mannoside 6-phosphates were compared with mannose-6-phosphate for their ability to inhibit contact sensitivity induced by picryl chloride.

In this experiment twenty CBA female mice were sensitised to picqyl chloride after the method of Enander et al., (22) by applying 200 µl of picryl chloride solution (0.5% in 95% ethanol) to an area (approximately 2 cm²) of their shaved abdomens. Seven days following sensitisation these animals were divided into four groups of five mice which bad been treated with either mannose-6-phosphate (55 mg/kg), methyl mannoside 6-phosphate (330 mg/kg) or decyl mannoside 6-phosphate (55 mg/kg) or saline (control) 30 minutes before they were challenged by applying 100 µl of picryl chloride solution (1% in 95% ethanol) to both sides of their left ears. Their right ears (control) were treated with 100 µl of 95% ethanol. Three and one half hours following challenge a second injection of drug or saline was given and this was repeated four times at 4 hour intervals. Four hours following the last injection the mice were anaesthetised (ether) and the contact sensitivity determined by comparing the thickness of the picryl chloride treated ears with those of the control ears. As shown in Table 3 the novel mannoside phosphates inhibited accumulation of inflammatory cells in challenged ears more effectively than mannose-6-phosphate.

TABLE 3

Novel mannoside 6-phosphates are effective in treatment of contact sensitivity when administered parentally.

| Mannose 6-phosphate or control substances | dose mg/kg/day | Injections No. | site | Number of mice | % swelling | % Inhibition of swelling[a] |
|---|---|---|---|---|---|---|
| saline control | — | 6 | s.c. | 5 | 100 | — |
| PEG 200 vehicle control | — | 6 | s.c. | 5 | 100 | — |
| mannose-6-P | 330 | 6 | s.c. | 5 | 83 | 17 |
| methyl mannoside 6-P | 330 | 6 | s.c. | 5 | 50 | 50 |
| decyl mannoside 6-P | 330 | 6 | s.c. | 5 | 23 | 77 |

EXAMPLE 13

The novel mannoside 6-phosphates have similar affinities for the mannose-6-phosphate receptor (insulin-like growth factor II or IGF-II receptor) as the natural ligand, mannose-6-phosphate. In order to assess the binding of the novel mannoside 6-phosphates to the M6P receptor a competitive binding assay was used. In this assay a fluorescein-labelled, polysaccharide (PPME) which contains abundant mannose-6-phosphate groups, was used to detect uptake through the M6P receptor on human monocytes (U937 cell line). PPME was isolated and purified by the method of Bretthauer et al., (23) from the exopolysaccharide secreted by the yeast *Pichia holstii*. (*P. holstii* strain American Type Culture Collection 13689, NRRL Y-2448, obtained from Centraalbureau voor Schimmel Cultures, Yeast Division, Julianalaan 67, Delft, The Netherlands). The PPME was fluoresceinated by a method based on that of Clabe et al. (24) in which the PPME was activated with cyanogen bromide and subsequently reacted with fluoreseinamine as follows: PPME (20 mg) was dissolved in water (1 ml), adjusted to pH 11 with 5 M NaOH and cyanogen bromide (10 mg) in water (0.2 ml) was then added and the mixture stirred for 5 minutes at room temperature. The mixture was then applied to a PD-10 desalting column (Pharmacia Fine Chemicals, Uppsala, Sweden), eluted with 0.2 M sodium borate buffer, pH 8, and the fraction containing the cyanogen-activated polysaccharide was reacted with an excess of fluoresceinamine (1 mg/ml) in the dark, over night at room temperature. Free fluoresceinamine was separated from the labelled polysaccharide by chromatograpy on a PD-10 column. Labelling efficiency was found to be 34 mM of fluorescein per mole of mannose.

The human monocyte cell line U937, which has a relatively high content of M6P receptors on its cell Surface (25), was obtained from the American Type Culture Collection (Rockville, Md.) and was maintained in RPMI 1640 medium (Gibco, Gaitersburg, Md.) supplemented with 2 mg/ml sodium bicarbonate, 0.2 mM glutamine, 30 $\mu$g/ml penicillin, 50 $\mu$g/ml streptamycin sulfate and 50 $\mu$g/ml neomycin sulfate and 10% foetal calf serum (FCS; Commonwealth Sarum Laboratories, Melbourne, Anstalia) at 37° C. (5% $CO_2$) in 75 $cm^2$ tissue culture flasks (Nurxc, Roskilde, Denmark). U937 cells were subcultured by inoculation into fresh medium at a density between $5\times10^4$ and $1\times10^5$ cells/ml, and were grown to a maximum density of $1\times10^6$ cells/mil. For the uptake assays U937 cell suspensions in 10% FCS/RPMI, were incubated with fluoresceinated-PPME (100 $\mu$g/ml), with or without inhibitors, for 60 minutes at 37° C. Adherent cells were released from flasks using 0.1% EDTA in PBS. Incubations were carried out in 96 well V-bottomed plastic microliter plates, at $1\times10^5$ cells in 40 $\mu$l volumes. Following incubations, the cells were washed twice with 10% FCS/RPMI and once with PBS and then fixed with 1% paraformaldehyde in PBS and analysed for fluorescence by flow cytometry. Background autofluorescence, determined from cells incubated with medium alone, was subtracted from all samples.

In order to demonstrate that attachment of the functional group at the oxygen in the 1-position of the phosphosugar moiety did not prevent binding of the mannoside 6-phosphate to the mannose-6-phosphate (IGF-II) receptor, several of the mannoside 6-phosphates with bulky groups attached at the 1-O position were screened in the above described assay and compared with mannose-6-phosphate, which is known to be a ligand and the principal binding moiety of the natural ligands for his receptor (26). As shown in FIG. I, the affinity of tile novel mannoside 6-phosphates for the receptor is similar to that of the natural ligand despite the introduction of bully fictional groups at the 1-position. Likewise the 1,6-hexamethylene di(mannoside 6-phosphate) is an effective inhibitor of binding of the natal ligand. In this experiment the non-phosphorylated sugar, mannose, was used as a control and the cells were analysed for fluorescence using a FACScan (Becton Dickinson, Mountain View, Calif.) and Lysys software. Cell populations were gated to exclude dead and aggregated cells and results expressed as median fluorescence intensity units (FIU).

Persons skilled in this art will appreciate that variations and modifications may be made to the invention as broadly described herein, other than those specifically described without departing from the spirit and scope of the invention. It is to be understood that this invention extends to include all such variations and modifications.

REFERENCES (1) Kornfeld, S. (1992). Structure and function of the mannose 6-phosphate/insulin-like growth factor II receptors. *Ann. Rev. Biochem.*, 61: 307–330.

(2) Dennis, P. A. and Rifkin, D. B. (1991). Cellular activation of latent transforming growth factor β requires binding to the cation-independent mannose 6-phosphate/ insulin like growth factor II receptor. *Proc. Natl. Acad. Sci. USA*, 88: 580–584.

(3) Braulke, T., Causin, C., Waheed, A., Junghans. U, Hasilik, A., Maly, P., Humbel, R. E., von-Figura, K. (1988). Mannose 6-phosphate/insulin-like growth factor II receptor: distinct binding sites for mannose 6-phosphate and insulin-like growth factor II. Biochem *Biophys. Res. Commun.*, 150: 1287–1293.

(4) Sporn, M. B. and Roberts, A. B. Transforming growth factor β. *J. Amer. Med. Assoc.*, 262; 938–941.

(5) Shah, M., Foreman, D. M. and Ferguson, M. W. (1992). Control of scarring in adult wounds by neutralising antibody to transforming growth factor beta. *Lancet*, 339: 213–214.

(6) Reynolds, D. D. and Evans, W. L. (1940). The synthesis of certain oligosaccharide acetates in the mannose series. *J. Amer. Chem. Soc.*, 62; 66–69.

(7) Hudson, C. S., Ness, R. K., Fletcher. H. G. Jr, (1950). The reaction of 2,3,4,6-tetrabenzoyl α-D-glucopyranoside bromide and 2,3,4,6-tetrabenzoyl α-D-mannopyranoside bromide with methanol. Certain benzoylated derivatives D-glucose and D-mannose. *J. Amer. Chem. Soc.*, 72: 2200–2205.

(8) Paterson, P. Y. (1976). In *Textbook of Immunopathology* (eds Miescher, P. A. and Mueller-Eberhard, H. J.) 179–213 (Grime & Stratton, New York, 1976).

(9) Alvord, E. C. Jr. (1984). In Experimental Allergic Encephalomyelitis: *A Useful Model for Multiple Sclerosis* (ed Alvord, E. C.), 1–511 (Liss, New York, 1984).

(10) Steiman, L. (1993). Autoimmune Disease. *Scientific American*, 269, 106–114.

(11) Raine, C. S., Barnett, L. B., Brown, A. and McFarlin, D. E. (1980). Neuropathology of experimental allergic encephalomyelitis in inbred strains of mice. *Lab. Invest.*, 43: 150–157.

(12) Paterson, P. Y., Day, E. D. and Whitacre, C. C. (1981). Neuroimmunologic diseases: Effector cell responses and immunoregalatory mechanisms. *Immunol. Rev.*, 55. 89–120.

(13) Waldor, M. K., Sriram, S., Hardy, R., Herzenberg, L. A., Herzenberg, L. A., Lanier, L., Lim, M. and Steinman, L. (1985). Reversal of experiment allergic encephalomyelitis with monoclonal antibody to a T-cell subset marker. *Science*, 227: 415–417.

(14) Holda, S. A. and Swanborg, R. H. Autoimune effector cells. (1982). II. Transfer of experimental allergic encephalomyelitis with a subset of T-lymphocytes. *Eur. J. Immunol*, 12: 453–455.

(15) Ben-Nun, A. and Cohen, I. R. (1982). Experimental autoimmune encephalomyelitis (EAE) mediated by T-cell lines: Process of selection of lines and characterization of the cells. J. Immunol. 129: 303–308.

(16) Anderson, J. R. (1988). Viral encephalitis and its pathology. *Current Topics in Pathology*, 76: 2340.

(17) Rabinowitz, S. G., Day, E. D., Paterson, P. Y. and Koenig, H. (1983). Endogenous myelin basic protein-serum factors (MBP-SFS) and anti-MBP antibodies in a patient with post-herpes simplex virus acute disseminated encephalomyelitis. *J. Neurol. Sci.*, 60: 393–400.

(18) Panitch, H. S. and McFarlin, D. E. (1977). Experimental allergic encephalomyelitis: enhancement of cell-mediated transfer by concanavalin A. *J. Immunol.*, 119: 1134–1137.

(19) Barnetson, R. St. C., and Gawkrodger, D., (1989). *Hypersensitivity—Type IV*. In: *Immunology*, (Eds. Roitt, I. M., Brostoff, J H and Male, D. K. Gower Medical Publishing, New York)

(20) Parish, C. R. (1972). Preferential induction of cell-mediated immunity by chemically modified sheep erytl-rocytes. *Eur. J. Immunol.,* 2: 143–151.
(21) Wing, E. J. and Remington, J. S. (1980). Delayed hypersensitivity and macrophage functions. In: *Basic and Clinical Immunology, Third Edition,* (Eds. H. H. Funderberg, D. P. Stites and J. V. Wells, Lange Medical Publications, Los Altos Calif.)
(22) Enander, I., Ahlstedlt, S., Nygren, H. and Bjsrksten, B. (1983). Sensitizing ability of derivatives of picryl chloride after exposure of mice on the skin and in the lung. *Int. Archs. Allergy Appl. Immun.,* 72: 59–66.
(23) Bretthauer, R. K., Kaczorowski, G. J. and Weise, M. J. (1973). Characterisation of a phosphorylated pentasaccharide isolated from *Hansenula holstii* Y-2448 phosphomannan. *Biochemistry,* 12: 1251.
(24) Glabe, C. G., Harty, P. K. and Rosen, S. D. (1983), Preparation and properties of fluorescent polysaccharides. *Anal. Biochem.* 130: 287.
(25) Bleekemolen, K. E., Stein, M., von Figura, K., Slot, J. W. and Geuze, H. J. (1988). The two mannose 6-phosphate receptors have almost identical subcellular distributions in (U937 monocytes. *Eur. J. Cell Biol.,* 47: 366–372.
(26) Hickman, S. and Neufleld, E. F. (1972), A hypothesis for I-cell disease: defective hydrolases that do not enter lysosomes. *Biochem. Biophys. Res Comm.,* 49: 992–999.
(27) Meldal, M. Christensen, M. K. and Bock. K. (1992). Large-scale synthesis of D-mannose-6-phosphate and other hexose 6-phosphates. *Carbohydrate Research,* 235:115–127.
(28) Gorin, P. A. J. and Perlin, A. S. (1961). Configuration of glycosidic linkages in oligosaccharides. IX Synthesis of α and β-D-mannopyranosyl disaccharides. *Can. J. Chem.* 39: 2472–2485.
(29) Wang, T. C., Kaegawa, H., Matsumoto, H. and Satoh, T. (1994). Influences of allylphenyl α-D-mannopyranosides an histamine release from rat peritoneal mast cells induced by concanavalin A. *Biol. Pharm. Bull.* 17:87–92.

What is claimed is:

1. A phosphosugar compound selected from:
   a. D-mannose-6-phosphate derivatives of the Formula I:

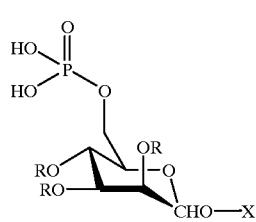

wherein the D-mannose-6-phosphate residue is in either the α-configuration or the β-configuration;
   and wherein X is selected from the group consisting of unsubstituted straight or branched chain alkyl, substituted straight or branched chain alkyl, unsubstituted straight or branched chain alkenyl, substituted straight or branched chain alkenyl, unsubstituted straight or branched chain alkynyl, substituted straight or branched chain alkynyl, unsubstituted cycloalkyl, substituted cycloalkyl, unsubstituted aryl, substituted aryl, unsubstituted heteroaryl, substituted heteroaryl, unsubstituted aralkyl, substituted aralkyl, unsubstituted heteroaralkyl, substituted heteroaralkyl, polyether, monosaccharide, disaccharide and trisaccharide groups;

and wherein each —OR group, which may be the same or different, is —OH or an ester group;
with the proviso that X does not represent methyl, butyl or hexadecyl when the —OR groups all represent —OH;
   b. D-mannose-6-phosphate derivatives of the Formula IA:

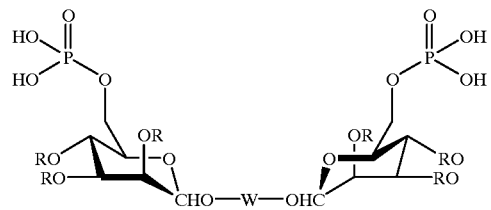

wherein the D-mannose-6-phosphate residues are in either the α-configuration or the β-configuration; wherein each —OR group is as defined above; and wherein W is a linker moiety between the residues, said linker moiety being selected from the group consisting of:
   (i) —(CH$_2$)$_n$—, in which n is an integer of from 2 to 20;
   (ii) —Z—, in which Z is selected from the group consisting of a substituted aryl or heteroaryl linker moiety and an unsubstituted aryl or heteroaryl linker moiety; and
   (iii) —(CH$_2$)$_n$—YZY—(CH$_2$)$_n$, in which n is an integer of from 1 to 10, Y is selected from the group consisting of O, NH, S, CO, CH$_2$, COO and CONH, and Z is selected from the group consisting of a substituted aryl or heteroaryl linker moiety and an unsubstituted aryl or heteroaryl linker moiety; and
   c. pharmaceutically acceptable salts thereof.

2. A method of treatment of cell-mediated inflammation in a human or non-human mammalian patient in need of such treatment, which comprises administration to the patient of an effective amount of at least one phosphosugar compound selected from:
   a. D-mannose-6-phosphate derivatives of the Formula I:

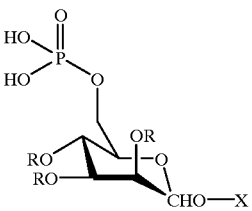

wherein the D-mannose-6-phosphate residue is in either the α-configuration or the β-configuration;
   and wherein X is selected from the group consisting of unsubstituted straight or branched chain alkyl, substituted straight or branched chain alkyl, unsubstituted straight or branched chain alkenyl, substituted straight or branched chain alkenyl, unsubstituted straight or branched chain alkynyl, substituted straight or branched chain alkynyl, unsubstituted cycloalkyl, substituted cycloalkyl, unsubstituted aryl, substituted aryl, unsubstituted heteroaryl, substituted heteroaryl, unsubstituted aralkyl, substituted aralkyl, unsubstituted heteroaralkyl, substituted heteroaralkyl, polyether, monosaccharide, disaccharide and trisaccharide groups;

and wherein each —OR group, which may be the same or different, is —OH or an ester group;

b. D-mannose-6-phosphate derivatives of the Formula IA:

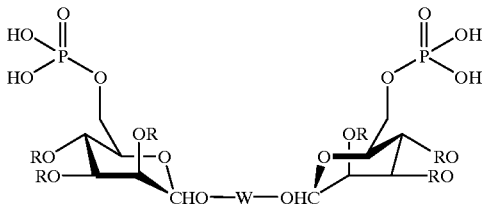

wherein the D-mannose-6-phosphate residues are in either the α-configuration or the β-configuration;

wherein each —OR group is as defined above; and wherein W is a linker moiety between the residues; and c. pharmaceutically acceptable salts thereof.

3. A phosphosugar compound according to claim 1 which is a compound of the Formula I, selected from the group consisting of propyl D-mannoside 6-phosphate;

pentyl D-mannoside 6-phosphate;

hexyl D-mannoside 6-phosphate;

heptyl D-mannoside 6-phosphate;

decyl D-mannoside 6-phosphate;

dodecyl D-mannoside 6-phosphate;

cyclohexylmethyl D-mannoside 6-phosphate;

cyclohexylethyl D-mannoside 6-phosphate;

phenyl D-mannoside 6-phosphate;

4-methoxyphenyl D-mannoside 6-phosphate;

benzyl D-mannoside 6-phosphate;

phenylethyl D-mannoside 6-phosphate; and pharmaceutically acceptable salts thereof.

4. A phosphosugar compound according to claim 1 which is a compound of the Formula IA, selected from the group consisting of 1,2-ethylene di(D-mannoside 6-phosphate);

1,6-hexameythylene di(D-mannoside 6-phosphate;

1,16-hexadecamethylene di(D-mannoside 6-phosphate);

1,4-phenylene di(D-mannoside 6-phosphate);

1,4-phenylenebisoxyethyl di(D-mannoside 6-phosphate); and pharmaceutically acceptable salts thereof.

5. A pharmaceutical or veterinary composition for anti-inflammatory treatment of a human or animal patient, which comprises at least one phosphosugar compound of claim 3 or claim 4, together with an acceptable pharmaceutical or veterinary carrier or diluent therefor.

6. A method of treatment of cell-mediated in a human or non-human mammalian patient of need of such treatment, which comprises administration to the patient of an effective amount of at least one phosphosugar compound of claim 3 or claim 4.

7. A method according to claim 6, wherein the treatment comprises treatment of cell-mediated inflammatory diseases.

8. A phosphosugar compound according to claim 1, wherein X is selected from the group consisting of a substituted, straight or branched chain alkyl group of from 1 to 20 carbon atoms, an unsubstituted straight or branched chain alkyl group of from 1 to 20 carbon atoms a substituted alkenyl or alkynyl group of from 2 to 20 carbon atoms, an unsubstituted alkenyl or alkynyl group of from 2 to 20 carbon atoms, a substituted aryl, heteroaryl, aralkyl or heteroaralkyl group, and an unsubstituted aryl, heteroaryl, aralkyl, or heteroaralkyl group.

9. A phosphosugar compound according to claim 1 or claim 8, wherein each —OR group is selected from the group consisting of —OH, a substituted acetyl group, and an unsubstituted acetyl group.

10. A phosphosugar compound according to claim 1, having the Formula II:

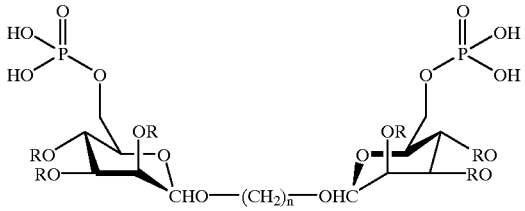

wherein each —OR group, which may be the same or different, is —OH or an ester group;

and n is an integer of from 2 to 20.

11. A phosphosugar compound according to claim 1, having the Formula III:

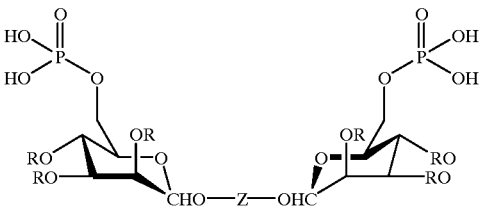

wherein each —OR group, which may be the same or different, is —OH or an ester group;

and Z is selected from the group consisting of a substituted aryl or heteroaryl linker moiety and an unsubstituted aryl or heteroaryl linker moiety.

12. A phosphosugar compound according to claim 1, having the Formula IV:

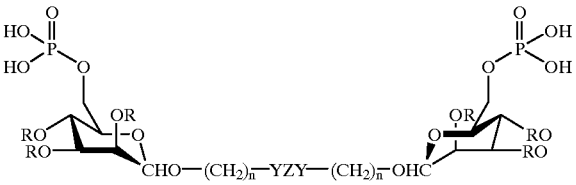

wherein each —OR group, which may be the same or different, is —OH or an ester group;

Y is selected from the group consisting of O, NH, S, CO, $CH_2$, COO and CONH;

Z is selected from the group consisting of a substituted aryl or heteroaryl linker moiety and an unsubstituted aryl or heteroaryl linker moiety;

and n is an integer of from 1 to 10.

13. A method according to claim 2, wherein the phosphosugar compound is a compound having the Formula II:

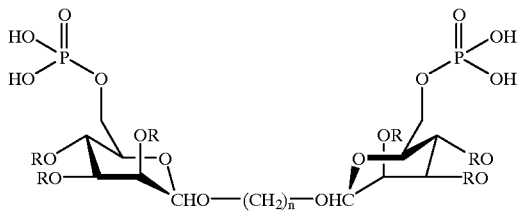

wherein each —OR group, which may be the same or different, is —OH or an ester group;
and n is an integer of from 2 to 20.

14. A method according to claim 2, wherein the phosphosugar compound is a compound having the Formula III:

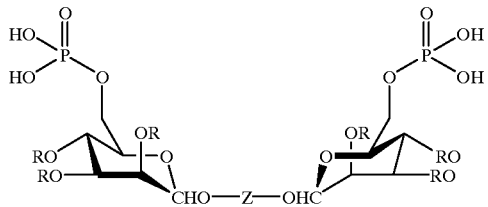

wherein each —OR group, which may be the same or different, is —OH or an ester group;
and Z is selected from the group consisting of a substituted aryl or heteroaryl linker moiety and an unsubstituted aryl or heteroaryl linker moiety.

15. A method according to claim 2, wherein the phosphosugar compound is a compound having the Formula IV:

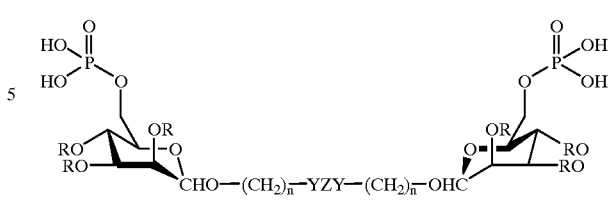

wherein each —OR group, which may be the same or different, is —OH or an ester group;

Y is selected from the group consisting of O, NH, S, CO, $CH_2$, COO and CONH;

Z is selected from the group consisting of a substituted aryl or heteroaryl linker moiety and an unsubstituted aryl or heteroaryl linker moiety;

and n is an integer from 1 to 10.

16. A method according to any of claims 2, 13, 14 and 15, wherein the treatment comprises treatment of cell-mediated inflammatory diseases.

17. A pharmaceutical or veterinary composition for anti-inflammatory treatment of a human or animal patient, which comprises at least one phosphosugar compound as defined in any of claims 2, 13, 14 and 15, together with an acceptable pharmaceutical or veterinary carrier or diluent therefor.

* * * * *